(12) United States Patent
Champ et al.

(10) Patent No.: US 7,923,479 B2
(45) Date of Patent: Apr. 12, 2011

(54) SUPERABSORBENT FOAM, METHOD FOR THE PRODUCTION THEREOF, AND USE THEREOF

(75) Inventors: Samantha Champ, Ludwigshafen (DE); Mariola Wanior, Erlensee (DE); Andreas Reifschneider, Mannheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 12/185,462

(22) Filed: Aug. 4, 2008

(65) Prior Publication Data
US 2009/0045138 A1 Feb. 19, 2009

Related U.S. Application Data

(63) Continuation of application No. 10/530,373, filed as application No. PCT/EP03/11013 on Oct. 6, 2003, now abandoned.

(30) Foreign Application Priority Data

Oct. 10, 2002 (DE) .................................. 102 47 241

(51) Int. Cl.
*C08G 18/48* (2006.01)
*C08J 9/00* (2006.01)
(52) U.S. Cl. .......................................................... 521/99
(58) Field of Classification Search .................... 521/50, 521/64, 79, 99
See application file for complete search history.

(56) References Cited

U.S. PATENT DOCUMENTS

| | | | |
|---|---|---|---|
| 4,813,945 A | | 3/1989 | Le-Khac |
| 5,230,959 A | | 7/1993 | Young, Sr. et al. |
| 5,338,766 A | * | 8/1994 | Phan et al. ...................... 521/63 |
| 5,849,405 A | * | 12/1998 | Wang et al. ................ 428/304.4 |
| 6,001,911 A | * | 12/1999 | Ishizaki et al. ................ 524/388 |
| 6,033,769 A | | 3/2000 | Brueggemann et al. |
| 6,136,873 A | | 10/2000 | Hahnle et al. |
| 6,245,410 B1 | | 6/2001 | Hahnle et al. |
| 6,455,600 B1 | | 9/2002 | Hahnle et al. |
| 6,657,101 B1 | * | 12/2003 | Malmgren et al. ............ 604/367 |
| 6,750,262 B1 | | 6/2004 | Hahnle et al. |
| 2002/0068494 A1 | | 6/2002 | Jackson et al. |
| 2003/0134918 A1 | * | 7/2003 | Ko et al. .......................... 521/50 |
| 2003/0153232 A1 | * | 8/2003 | Raidel et al. .................. 442/417 |
| 2005/0007616 A1 | | 1/2005 | Sugiyama et al. |
| 2005/0176834 A1 | | 8/2005 | Hintz et al. |

FOREIGN PATENT DOCUMENTS

| | | |
|---|---|---|
| DE | 102 04 980.7 | 2/2002 |
| EP | 0 264 208 | 4/1988 |
| EP | 0 436 514 | 7/1991 |
| EP | 693525 A2 * | 1/1996 |
| EP | 0 858 478 | 8/1998 |
| WO | WO-97/31600 | 9/1997 |
| WO | WO-97/31971 | 9/1997 |
| WO | WO-99/44648 | 9/1999 |
| WO | WO-00/52087 | 9/2000 |

OTHER PUBLICATIONS

Machine Translation of EP0693525.*

* cited by examiner

*Primary Examiner* — Mark Eashoo
*Assistant Examiner* — Angela C Scott
(74) *Attorney, Agent, or Firm* — Marshall, Gerstein & Borun LLP

(57) ABSTRACT

Superabsorbent foam comprising superabsorbent fiber and/or fruit fiber, processes for producing superabsorbent foam having improved wet strength by foaming a crosslinkable aqueous mixture comprising at least 50 mol % neutralized acid-functional monoethylenically unsaturated monomer or at least one basic polymer, crosslinker, superabsorbent synthetic fiber and/or fruit fiber and at least one surfactant and subsequently polymerizing the monomer in the foamed mixture or crosslinking the basic polymer to form a hydrogel foam and use of the thus obtainable foam in hygiene articles to absorb body fluids, in dressing material to cover wounds, as a sealing material, as a packaging material, as a soil improver, as a soil substitute, to dewater sludges, to thicken waterborne paints or coatings in the course of disposing of residual quantities thereof, to dewater water-containing oils or hydrocarbons or as a material for filters in ventilation systems.

15 Claims, 2 Drawing Sheets

US 7,923,479 B2

SUPERABSORBENT FOAM, METHOD FOR THE PRODUCTION THEREOF, AND USE THEREOF

CROSS-REFERENCE TO RELATED APPLICATION

This is a continuation of U.S. patent application Ser. No. 10/530,373, filed Apr. 6, 2005, pending, which claims the benefit of International Application No. PCT/EP2003/011013, filed Oct. 6, 2003, which claims the benefit of German patent application No. 102 47 241.6, filed Oct. 10, 2002.

DESCRIPTION

This invention relates to superabsorbent foam obtainable by foaming a polymerizable aqueous mixture and polymerizing the foamed mixture, a process for producing superabsorbent foam and the use of the foam in hygiene articles to absorb body fluids.

Water-absorbent, predominantly open-cell foams based on crosslinked acid-functional monomers are known, cf EP-B-0 858 478, WO-A-99/44648 and WO-A-00/52087. They are produced for example by foaming a polymerizable aqueous mixture which comprises at least 50 mol % neutralized acid-functional monoethylenically unsaturated monomer, crosslinker and at least one surfactant and subsequently polymerizing the foamed mixture. The foaming of the polymerizable mixture may be effected for example by dispersing fine bubbles or a radical-inert gas or by dissolving such a gas under elevated pressure in the polymerizable mixture and decompressing the mixture. The water content of the foams is adjusted to 1-60% by weight for example. The foams may optionally be subjected to surface postcrosslinking by spraying a crosslinker onto the foamed material or immersing the foam therein and heating the crosslinker-laden foam to a higher temperature. The foams are used for example in hygiene articles to acquire, distribute and store body fluids.

WO-A-97/31600 discloses an absorber element for use in hygiene or sanitary articles which has a plurality of elements composed of a superabsorbent foam arranged on a support in a grid pattern at distances so that the elements in the swollen state touch at their peripheries. It is possible for example for a monomer foam to be applied to the support in the desired grid pattern and subsequently polymerized on the support or for separately produced foam elements to be chemically or physically fixed on the support in the desired grid pattern. However, the wet strength of the above-described superabsorbent foams is in need of improvement.

Known superabsorbent fiber is obtainable for example by neutralizing the carboxyl groups of a hydrolyzed copolymer of isobutene and maleic anhydride with aqueous sodium hydroxide solution to 20-80%, adding a bifunctional compound capable of reacting with the nonneutralized carboxyl groups of copolymer, eg propylene glycol or ethanolamine, and then substantially removing the water from the solution to leave the solution with a solids content of 45%. This solution is subsequently spun into fiber. The fiber is thereafter heated to a comparatively high temperature, for example 210° C., to crosslink the copolymer. The crosslinked copolymer has superabsorbent properties. It is used for example in baby diapers, tampons, sanitary napkins, surgical sponges and dressings to absorb body fluids. Such superabsorbent fiber is known, cf for example EP-B-0 264 208, EP-B-0 272 072, EP-B-0 436 514 and U.S. Pat. No. 4,813,945.

Prior DE application 102 04 980.7, unpublished at the priority date of the present invention, discloses foams of water-absorbing basic polymer which are obtainable by foaming an aqueous mixture comprising at least one basic polymer such as polyvinylamine and at least one crosslinker such as glycidyl ether and then crosslinking the foamed mixture. The wet strength of the water-absorbing foams thus obtainable is likewise in need of improvement.

It is an object of the present invention to improve the wet strength of the water-absorbing foam.

We have found that this object is achieved according to the invention by superabsorbent foam comprising superabsorbent synthetic fiber and/or natural fiber selected from the group consisting of apple fiber, orange fiber, tomato fiber, wheat fiber and/or oat fiber. Such foam is obtainable by foaming a polymerizable aqueous mixture comprising at least 50 mol % neutralized acid-functional monoethylenically unsaturated monomer or at least one basic polymer, crosslinker, superabsorbent fiber and at least one surfactant and subsequently polymerizing and/or crosslinking the foamed mixture.

The present invention also provides a process for producing superabsorbent foam having improved wet strength, which comprises foaming a crosslinkable aqueous mixture comprising at least 50 mol % neutralized acid-functional monoethylenically unsaturated monomer or at least one basic polymer, crosslinker, superabsorbent synthetic fiber and/or natural fiber selected from the group consisting of apple fiber, orange fiber, tomato fiber, wheat fiber and/or oat fiber and at least one surfactant and subsequently polymerizing the monomer in the foamed mixture or crosslinking the basic polymer to form a hydrogel foam.

Foams based on crosslinked acid-functional addition polymers are known from the cited prior art references EP-B-0 858 478 page 2 line 55 to page 18 line 22, WO-A-99/44648 and WO-A-00/52087 page 5 line 23 to page 41 line 18. The known processes comprise initially foaming an aqueous mixture which comprises for example a) from 10 to 80% by weight of acid-functional monoethylenically unsaturated monomer which is at least 50 mol % neutralized,
b) optionally up to 50% by weight of other monoethylenically unsaturated monomer,
c) from 0.001 to 5% by weight of crosslinker,
d) initiators,
e) from 0.1 to 20% by weight of at least one surfactant,
f) optionally a solubilizer, and
g) optionally thickeners, foam stabilizers, polymerization regulators, fillers and/or cell nucleators.

However, it is also possible to foam an aqueous mixture which, instead of said monomers (a) and (b), contains a basic polymer whose basic groups have optionally been partly neutralized. The aqueous mixtures can be foamed for example by dispersing fine bubbles of radical-inert gas in the mixture or dissolving such a gas in the crosslinkable mixture at from 2 to 400 bar and subsequently decompressing the mixture to atmospheric. This provides a flowable foam which can be filled into molds or cured on a belt. Curing is effected by addition polymerization when acid-functional monomers, optionally other monoethylenically unsaturated monomers and crosslinkers are used and by crosslinking when basic polymers are used.

BASIC POLYMERS

Figure 1:
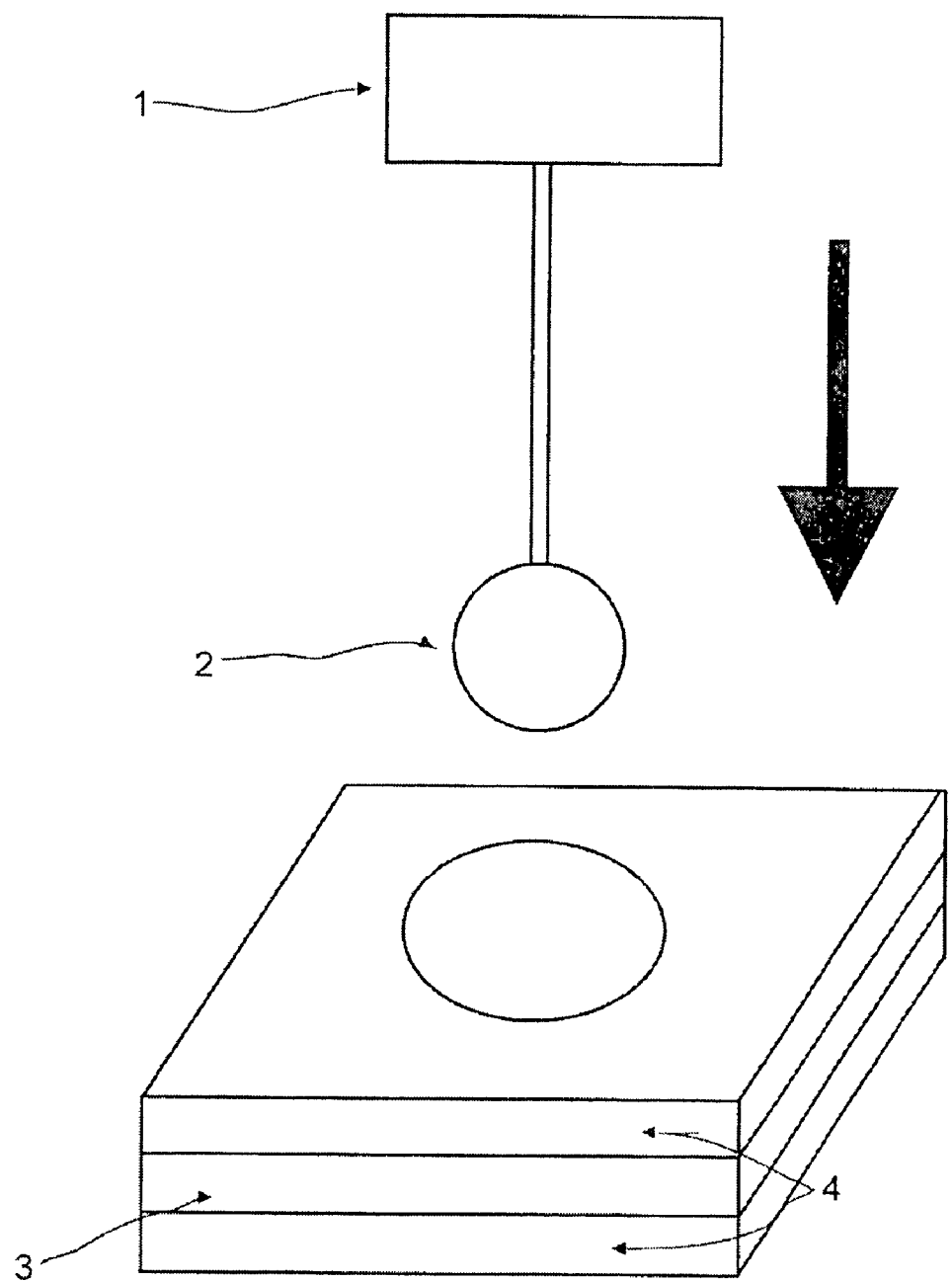
FIGS. 1 and 2 are schematic diagrams of an instrument for measuring a Wet Failure Value (WFV) of a superabsorbent foam.

Useful basic polymers include for example polymers containing vinylamine units, polymers containing vinylguanidine units, polymers containing dialkylaminoalkyl(meth)acrylamide units, polyethyleneimines, ethyleneimine-grafted polyamidoamines and polydiallyldimethylammonium chlorides.

Polymers containing vinylamine units are known, of U.S. Pat. No. 4,421,602, U.S. Pat. No. 5,334,287, EP-A-0 216 387, U.S. Pat. No. 5,981,689, WO-A-00/63295 and U.S. Pat. No. 6,121,409. They are prepared by hydrolysis of polymers containing open-chain N-vinylcarboxamide units. These polymers are obtainable for example by polymerizing N-vinylformamide, N-vinyl-N-methylformamide, N-vinylacetamide, N-vinyl-N-methylacetamide, N-vinyl-N-ethylacetamide and N-vinylpropionamide. The monomers mentioned can be polymerized either alone or together with other monomers.

Useful monoethylenically unsaturated monomers for copolymerization with the N-vinylcarboxamides include all compounds copolymerizable therewith. Examples thereof are vinyl esters of saturated carboxylic acids of 1 to 6 carbon atoms such as vinyl formate, vinyl acetate, vinyl propionate and vinyl butyrate and vinyl ethers such as $C_1$-$C_6$-alkyl vinyl ethers, for example methyl vinyl ether or ethyl vinyl ether. Useful comonomers further include esters, amides and nitriles of ethylenically unsaturated $C_3$-$C_6$-carboxylic acids, for example methyl acrylate, methyl methacrylate, ethyl acrylate and ethyl methacrylate, acrylamide and methacrylamide and also acrylonitrile and methacrylonitrile.

Useful carboxylic esters are further derived from glycols or polyalkylene glycols, in either case only one OH group being esterified, for example hydroxyethyl acrylate, hydroxyethyl methacrylate, hydroxypropyl acrylate, hydroxybutyl acrylate, hydroxypropyl methacrylate, hydroxybutyl methacrylate and also acrylic monoesters of polyalkylene glycols having a molar mass from 500 to 10 000. Useful comonomers further include esters of ethylenically unsaturated carboxylic acids with amino alcohols such as for example dimethylaminoethyl acrylate, dimethylaminoethyl methacrylate, diethylaminoethyl acrylate, diethylaminoethyl methacrylate, dimethylaminopropyl acrylate, dimethylaminopropyl methacrylate, diethylaminopropyl acrylate, dimethylaminobutyl acrylate and diethylaminobutyl acrylate. The basic acrylates can be used in the form of the free bases, in the form of their salts with mineral acids such as hydrochloric acid, sulfuric acid or nitric acid, in the form of their salts with organic acids such as formic acid, acetic acid, propionic acid or sulfonic acids or in quaternized form. Useful quaternizing agents include for example dimethyl sulfate, diethyl sulfate, methyl chloride, ethyl chloride or benzyl chloride.

Useful comonomers further include amides of ethylenically unsaturated carboxylic acids such as acrylamide, methacrylamide and also N-alkylmonoamides and -diamides of monoethylenically unsaturated carboxylic acids having alkyl moieties of 1 to 6 carbon atoms, for example N-methylacrylamide, N,N-dimethylacrylamide, N-methylmethacrylamide, N-ethylacrylamide, N-propylacrylamide and tert-butylacrylamide and also basic (meth)acrylamides, for example dimethylaminoethylacrylamide, dimethylaminoethylmethacrylamide, diethylaminoethylacrylamide, diethylaminoethylmethacrylamide, dimethylaminopropylacrylamide, diethylaminopropylacrylamide, dimethylaminopropylmethacrylamide and diethylaminopropylmethacrylamide.

Useful comonomers further include N-vinylpyrrolidone, N-vinylcaprolactam, acrylonitrile, methacrylonitrile, N-vinylimidazole and also substituted N-vinylimidazoles such as for example N-vinyl-2-methylimidazole, N-vinyl-4-methylimidazole, N-vinyl-5-methylimidazole, N-vinyl-2-ethylimidazole and N-vinylimidazolines such as N-vinylimidazoline, N-vinyl-2-methylimidazoline and N-vinyl-2-ethylimidazoline. N-Vinylimidazoles and N-vinylimidazolines are used not only in the form of the free bases but also after neutralization with mineral acids or organic acids or in quaternized form, in which case the quaternization is preferably effected using dimethyl sulfate, diethyl sulfate, methyl chloride or benzyl chloride. It is further possible to use diallyldialkylammonium halides, for example diallyldimethylammonium chloride.

The copolymers contain for example
from 95 to 5 mol % and preferably from 90 to 10 mol % of at least one N-vinylcarboxamide, and
from 5 to 95 mol %, and preferably from 10 to 90 mol % of other monoethylenically unsaturated monomers copolymerizable therewith in copolymerized form. The comonomers are preferably free of acid groups.

To prepare polymers containing vinylamine units, it is preferable to start from homopolymers of N-vinylformamide or from copolymers obtainable by copolymerizing
N-vinylformamide with
vinyl formate, vinyl acetate, vinyl propionate, acrylonitrile, N-vinylcaprolactam, N-vinylurea, N-vinylpyrrolidone or $C_1$-$C_6$-alkyl vinyl ethers and subsequently hydrolyzing the homo- or copolymers to form vinylamine units from the copolymerized N-vinylformamide units, the degree of hydrolysis being for example in the range from 5 to 100 mol % and preferably in the range from 70 to 100 mol %. The hydrolysis of the above-described polymers is effected according to known processes by the action of acids, bases or enzymes. When acids are used as a hydrolyzing agent, the vinylamine units of the polymers are present as an ammonium salt, whereas the hydrolysis with bases gives rise to free amino groups.

The degree of hydrolysis of the homopolymers of the N-vinylcarboxamides and their copolymers can be in the range from 5 to 100 mol % and is preferably in the range from 70 to 100 mol %. In most cases, the degree of hydrolysis of the homo- and copolymers is in the range from 80 to 95 mol %. The degree of hydrolysis of the homopolymers is equivalent to the level of vinylamine units in the polymers. In the case of copolymers which contain vinyl esters in copolymerized form, the hydrolysis of the N-vinylformamide units may be accompanied by a hydrolysis of the ester groups to form vinyl alcohol units. This is particularly the case when the hydrolysis of the copolymers is conducted in the presence of aqueous sodium hydroxide solution. Polymerized units of acrylonitrile will likewise undergo chemical changes in the course of the hydrolysis, producing for example amide groups or carboxyl groups. The homo- and copolymers containing vinylamine units may contain up to 20 mol % of amidine units, for example due to a reaction of formic acid with two adjacent amino groups or due to intramolecular reaction of an amino group with an adjacent amide group, for example of copolymerized N-vinylformamide. The molar masses of the polymers containing vinylamine units range for example from 500 to 10 million and preferably from 1000 to 5 million (determined by light scattering). This molar mass range corresponds for example to K values from 5 to 300 and preferably from 10 to 250 (determined after H. Fikentscher in 5% aqueous sodium chloride solution at 25° C. and at a polymer concentration of 0.5% by weight).

The polymers containing vinylamine units are preferably used in salt-free form. Salt-free aqueous solutions of polymers containing vinylamine units are preparable for example from the above-described salt-containing polymer solutions by ultrafiltration using suitable membranes having molecular weight cutoffs at for example from 1000 to 500 000 dalton and preferably at from 10 000 to 300 000 dalton. Similarly, the hereinbelow described aqueous solutions of other polymers containing amino and/or ammonium groups can be obtained in salt-free form by ultrafiltration.

Similarly, derivatives of polymers containing vinylamine units can be used as polymers forming basic hydrogels. For instance, polymers containing vinylamine units can be subjected to amidation, alkylation, sulfonamide formation, urea formation, thiourea formation, carbamate formation, acylation, carboxymethylation, phosphonomethylation or Michael addition of the amino groups of the polymer to prepare a multiplicity of suitable hydrogel derivatives. Of particular interest here are uncrosslinked polyvinylguanidines which are accessible by reaction of polymers containing vinylamine units, preferably polyvinylamines, with cyanamide ($R^1R^2N$—CN where $R^1$, $R^2$=H, C1-C4-alkyl, C3-C6-cycloalkyl, phenyl, benzyl, alkyl-substituted phenyl or naphthyl) cf U.S. Pat. No. 6,087,448 column 3 line 64 to column 5 line 14.

Polymers containing vinylamine units further include hydrolyzed graft polymers of for example N-vinylformamide on polyalkylene glycols, polyvinyl acetate, polyvinyl alcohol, polyvinylformamides, polysaccharides such as starch, oligosaccharides or monosaccharides. The graft polymers are obtainable for example by free-radically polymerizing N-vinylformamide in an aqueous medium in the presence of at least one of the grafting bases mentioned, optionally together with copolymerizable other monomers, and subsequently hydrolyzing the engrafted vinylformamide units in a known manner to obtain vinylamine units.

Useful for the preparation of polymers water-absorbing basic polymers further include polymers of dialkylaminoalkyl(meth)acrylamides. Useful monomers for preparing such polymers include for example dimethylaminoethylacrylamide, dimethylaminoethylmethacrylamide, dimethylaminopropylacrylamide, dimethylaminopropylmethacrylamide, diethylaminoethylacrylamide, diethylaminoethylmethacrylamide and diethylaminopropylacrylamide. These monomers may be used in the form of the free bases, as salts with inorganic or organic acids or in quaternized form in the polymerization. They may be free-radically polymerized to homopolymers or together with other copolymerizable monomers to copolymers. The polymers contain for example at least 30 mol % and preferably at least 70 mol % of the basic monomers mentioned. Water-absorbing basic polymers based on poly(dimethylaminoalkylacrylamide)s are known from U.S. Pat. No. 5,962,578.

Useful basic polymers further include polyethyleneimines, which are preparable for example by polymerization of ethyleneimine in aqueous solution in the presence of acid-detaching compounds, acids or Lewis acids as a catalyst. Polyethyleneimines have for example molar masses of up to 2 million and preferably from 200 to 1 000 000. Particular preference is given to using polyethyleneimines having molar masses from 500 to 750 000. The polyethyleneimines may optionally be modified, for example alkoxylated, alkylated or amidated. They may also be subjected to a Michael addition or a Strecker synthesis. The polyethyleneimine derivatives obtainable thereby are likewise useful as basic polymers for preparing water-absorbing basic polymers.

Useful basic polymers further include ethyleneimine-grafted polyamidoamines, which are obtainable for example by condensing dicarboxylic acids with polyamines and subsequently grafting with ethyleneimine. Useful polyamidoamines are obtained for example by reacting dicarboxylic acids having 4 to 10 carbon atoms with polyalkylenepolyamines containing 3 to 10 basic nitrogen atoms in the molecule. Examples of dicarboxylic acids are succinic acid, maleic acid, adipic acid, glutaric acid, suberic acid, sebacic acid and terephthalic acid. Polyamidoamines may also be prepared using mixtures of dicarboxylic acids and likewise using mixtures of a plurality of polyalkylenepolyamines. Useful polyalkylenepolyamines include for example diethylenetriamine, triethylenetetramine, tetraethylenepentamine, dipropylenetriamine, tripropylenetetramine, dihexamethylenetriamine, aminopropylethylenediamine and bisaminopropylethylenediamine. To prepare polyamidoamines, the dicarboxylic acids and polyalkylenepolyamines are heated to comparatively high temperatures, for example to temperatures in the range from 120 to 220° C. and preferably in the range from 130 to 180° C. The water formed in the course of the condensation is removed from the system. The condensation may optionally also utilize lactones or lactams of carboxylic acids having 4 to 8 carbon atoms. The amount of polyalkylenepolyamine used per mole of a dicarboxylic acid is for example in the range from 0.8 to 1.4 mol. These polyamidoamines are grafted with ethyleneimine. The grafting reaction is carried out for example in the presence of acids or Lewis acids such as sulfuric acid or boron trifluoride etherates at for example from 80 to 100° C. Compounds of this kind are described in DE-B-24 34 816 for example.

Useful basic polymers further include the optionally crosslinked polyamidoamines, which may optionally additionally have been grafted with ethyleneimine prior to any crosslinking. The crosslinked ethyleneimine-grafted polyamidoamines are water soluble and have for example an average molecular weight from 3000 to 2 million dalton. Customary crosslinkers include for example epichlorohydrin or bischlorohydrin ethers of alkylene glycols and polyalkylene glycols.

Useful basic polymers further include polyallylamines. Polymers of this kind are obtained by homopolymerizing of allylamine, preferably in acid-neutralized form, or by copolymerizing allylamine with other monoethylenically unsaturated monomers described above as comonomers for N-vinylcarboxamides.

Useful basic polymers further include water-soluble crosslinked polyethyleneimines which are obtainable by reaction of polyethyleneimines with crosslinkers such as epichlorohydrin or bischlorohydrin ethers of polyalkylene glycols having from 2 to 100 ethylene oxide and/or propylene oxide units and which still have free primary and/or secondary amino groups. Also suitable are amidic polyethyleneimines which are obtainable for example by amidation of polyethyleneimines with $C_1$-$C_{22}$-monocarboxylic acids.

Useful cationic polymers further include alkylated polyethyleneimines and alkoxylated polyethyleneimines. The polyethyleneimine is alkoxylated using for example from 1 to 5 ethylene oxide or propylene oxide units per NH unit in the polyethyleneimine.

The abovementioned basic polymers have for example K values from 8 to 300 and preferably from 15 to 180 (determined after H. Fikentscher in 5% aqueous sodium chloride solution at 25° C. and a polymer concentration of 0.5% by weight). At pH 4.5 their charge density is for example not less than 1 and preferably not less than 4 meq/g of polyelectrolyte.

Preferred basic polymers include polymers containing vinylamine units, polyvinylguanidines and polyethyleneimines. Examples thereof are:

vinylamine homopolymers, 10-100% hydrolyzed polyvinylformamides, partially or completely hydrolyzed copolymers of vinylformamide and vinyl acetate, vinyl alcohol, vinylpyrrolidone or acrylamide each having molar masses of 3000-2 000 000 and also polyethyleneimines, crosslinked polyethyleneimines or amidated polyethyleneimines which each have molar masses from 500 to 3 000 000. The polymer content of the aqueous solution is for example from 1 to 60%, preferably from 2 to 15% and usually from 5 to 10% by weight.

Crosslinkers

To convert the above-described basic polymers into water-absorbing basic polymers, they are reacted with at least one crosslinker. The basic polymers are usually soluble or readily dispersible in water. Crosslinking is therefore mainly carried out in an aqueous medium. Preference is given to using aqueous solutions of basic polymers that have been desalted, for example by ultrafiltration, or whose neutral salt content is below 1% or below 0.5% by weight. The crosslinkers have at least two reactive groups capable of reacting with the amino groups of the basic polymers to form insoluble products which are water-absorbing polymers. The amount of crosslinker used per 1 part by weight of basic polymer is for example in the range from 0.1 to 50 parts by weight, preferably in the range from 1 to 5 parts by weight and especially in the range from 1.5 to 3 parts by weight. Useful crosslinkers are described in WO-A-00/63295 page 14 line 43 to page 21 line 5.

Useful bi- or polyfunctional crosslinkers include for example (1) di- and polyglycidyl compounds
(2) di- and polyhalogen compounds
(3) compounds having two or more isocyanate groups, which may be blocked
(4) polyaziridines
(5) carbonic acid derivatives
(6) compounds having two or more activated double bonds capable of undergoing a Michael addition
(7) di- and polycarboxylic acids and acid derivatives thereof
(8) monoethylenically unsaturated carboxylic acids, esters, amides and anhydrides
(9) di- and polyaldehydes and di- and polyketones.

Preferred crosslinkers (1) are for example the bischlorohydrin ethers of polyalkylene glycols described in U.S. Pat. No. 4,144,123. Phosphoric acid diglycidyl ether and ethylene glycol diglycidyl ether are also suitable.

Further crosslinkers are the products of reacting at least trihydric alcohols with epichlorohydrin to form reaction products having at least two chlorohydrin units, polyhydric alcohols used being for example glycerol, ethoxylated or propoxylated glycerols, polyglycerols having 2 to 15 glycerol units in the molecule and also optionally ethoxylated and/or propoxylated polyglycerols. Crosslinkers of this type are known from DE-A-2 916 356 for example.

Useful crosslinkers (2) are α,ω- or vicinal dichloroalkanes, for example 1,2-dichloroethane, 1,2-dichloropropane, 1,3-dichlorobutane and 1,6-dichlorohexane.

Furthermore, EP-A-0 025 515 discloses α,ω-dichloropolyalkylene glycols having preferably 1-100, especially 1-100 ethylene oxide, units for use as crosslinkers.

Useful crosslinkers further include crosslinkers (3) which contain blocked isocyanate groups, for example trimethyl-hexamethylene diisocyanate blocked with 2,2,6,6_tetramethylpiperidin-4-one. Such crosslinkers are known; cf for example from DE-A-4 028 285.

Preference is further given to crosslinkers (4) which contain aziridine units and are based on polyethers or substituted hydrocarbons, for example 1,6-bis-N-aziridino methane, cf U.S. Pat. No. 3,977,923. This class of crosslinkers further includes products formed by reacting dicarboxylic esters with ethyleneimine and containing at least two aziridino groups, and mixtures of the crosslinkers mentioned.

Useful halogen-free crosslinkers of group (4) include reaction products prepared by reacting ethyleneimine with dicarboxylic esters completely esterified with monohydric alcohols of from 1 to 5 carbon atoms. Examples of suitable dicarboxylic esters are dimethyl oxalate, diethyl oxalate, dimethyl succinate, diethyl succinate, dimethyl adipate, diethyl adipate and dimethyl glutarate. For instance, reacting diethyl oxalate with ethyleneimine gives bis[β-(1-aziridino)ethyl]oxalamide. Dicarboxylic esters are reacted with ethyleneimine in a molar ratio of 1: at least 4. The reactive groups of these crosslinkers are the terminal aziridine groups. These crosslinkers may be characterized for example with the aid of the formula:

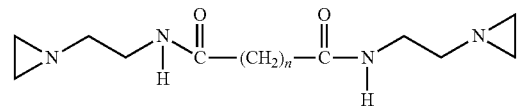

where n is from 0 to 22.

Illustrative of crosslinkers (5) are ethylene carbonate, propylene carbonate, urea, thiourea, guanidine, dicyandiamide or 2-oxazolidinone and its derivatives. Of this group of monomers, preference is given to using propylene carbonate, urea and guanidine.

Crosslinkers (6) are reaction products of polyetherdiamines, alkylenediamines, polyalkylenepolyamines, alkylene glycols, polyalkylene glycols or mixtures thereof with monoethylenically unsaturated carboxylic acids, esters, amides or anhydrides of monoethylenically unsaturated carboxylic acids, which reaction products contain at least two ethylenically unsaturated double bonds, carboxamide, carboxyl or ester groups as functional groups, and also methylenebisacrylamide and divinyl sulfone.

Crosslinkers (6) are for example reaction products of polyetherdiamines having preferably from 2 to 50 alkylene oxide units, alkylenediamines such as ethylenediamine, propylenediamine, 1,4-diaminobutane and 1,6-diaminohexane, polyalkylenepolyamines having molecular weights <5000 for example diethylenetriamine, triethylenetetramine, dipropylenetriamine, tripropylenetetramine, dihexamethylenetriamine and aminopropylethylenediamine, alkylene glycols, polyalkylene glycols or mixtures thereof with monoethylenically unsaturated carboxylic acids,
    esters of monoethylenically unsaturated carboxylic acids,
    amides of monoethylenically unsaturated carboxylic acids, and
    anhydrides of monoethylenically unsaturated carboxylic acids.

These reaction products and their preparation are described in EP-A-873 371 and are expressly mentioned for use as crosslinkers.

Particularly preferred crosslinkers are the therein mentioned reaction products of maleic anhydride with α,ω-polyetherdiamines having a molar mass of from 400 to 5000, the reaction products of polyethyleneimines having a molar mass of from 129 to 50 000 with maleic anhydride and also the reaction products of ethylenediamine or triethylenetetramine with maleic anhydride in a molar ratio of 1: at least 2.

Crosslinkers (6) are preferably compounds of the formula

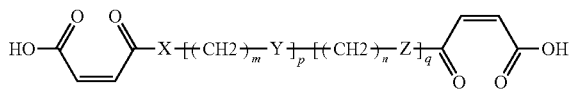

where X, Y, Z=O, NH and Y is additionally CH$_2$ m, n=0-4 p, q=0-45000 which are obtainable by reacting polyetherdiamines, ethylenediamine or polyalkylenepolyamines with maleic anhydride.

Further halogen-free crosslinkers of group (7) are at least dibasic saturated carboxylic acids such as dicarboxylic acids and also the salts, diesters and diamides derived therefrom. These compounds may be characterized for example by means of the formula

where X=OH, OR$^1$, N(R$^2$)$_2$

R$^1$=C$_1$-C$_{22}$-alkyl,

R$^1$=H, C$_1$-C$_{22}$-alkyl and n=0-22.

As well as dicarboxylic acids of the abovementioned formula it is possible to use, for example, monoethylenically unsaturated dicarboxylic acids such as maleic acid or itaconic acid. The esters of the contemplated dicarboxylic acids are preferably derived from alcohols having from 1 to 4 carbon atoms. Examples of suitable dicarboxylic esters are dimethyl oxalate, diethyl oxalate, diisopropyl oxalate, dimethyl succinate, diethyl succinate, diisopropyl succinate, di-n-propyl succinate, diisobutyl succinate, dimethyl adipate, diethyl adipate and diisopropyl adipate or Michael addition products which contain at least two ester groups and are formed from polyetherdiamines, polyalkylenepolyamines or ethylenediamine and esters of acrylic acid or methacrylic acid with, in each case, monohydric alcohols of from 1 to 4 carbon atoms. Examples of suitable esters of ethylenically unsaturated dicarboxylic acids are dimethyl maleate, diethyl maleate, diisopropyl maleate, dimethyl itaconate and diisopropyl itaconate. It is also possible to use substituted dicarboxylic acids and their esters such as tartaric acid (D,L-form and as racemate) and also tartaric esters such as dimethyl tartrate and diethyl tartrate.

Examples of suitable dicarboxylic anhydrides are maleic anhydride, itaconic anhydride and succinic anhydride. Useful crosslinkers (7) further include for example dimethyl maleate, diethyl maleate and maleic acid. The crosslinking of amino-containing compounds with the aforementioned crosslinkers takes place with the formation of amide groups or, in the case of amides such as adipamide, by transamidation. Maleic esters, monoethylenically unsaturated dicarboxylic acids and their anhydrides can bring about crosslinking both by formation of carboxamide groups and by addition of NH groups of the component to be crosslinked (polyamidoamines, for example) in the manner of a Michael addition.

The at least dibasic saturated carboxylic acids of crosslinker class (7) include for example tri- and tetracarboxylic acids such as citric acid, propanetricarboxylic acid, nitrilotriacetic acid, ethylenediaminetetraacetic acid, butanetetracarboxylic acid and diethylenetriaminepentaacetic acid. Useful crosslinkers of group (7) further include the salts, esters, amides and anhydrides derived from the aforementioned carboxylic acids, e.g., dimethyl tartrate, diethyl tartrate, dimethyl adipate and diethyl adipate.

Useful crosslinkers of group (7) further include polycarboxylic acids obtainable by polymerizing monoethylenically unsaturated carboxylic acids, anhydrides, esters or amides. Examples of suitable monoethylenically unsaturated carboxylic acids are acrylic acid, methacrylic acid, fumaric acid, maleic acid and/or itaconic acid. Examples of useful crosslinkers are accordingly polyacrylic acids, copolymers of acrylic acid and methacrylic acid or copolymers of acrylic acid and maleic acid. Illustrative comonomers are vinyl ether, vinyl formate, vinyl acetate and vinyllactam.

Further useful crosslinkers (7) are prepared for example by free-radical polymerization of anhydrides such as maleic anhydride in an inert solvent such as toluene, xylene, ethylbenzene, isopropylbenzene or solvent mixtures. Besides the homopolymers, copolymers of maleic anhydride are suitable, for example copolymers of acrylic acid and maleic anhydride or copolymers of maleic anhydride and a C$_2$- to C$_{30}$-olefin.

Examples of preferred crosslinkers (7) are copolymers of maleic anhydride and isobutene or copolymers of maleic anhydride and diisobutene. Copolymers containing anhydride groups may optionally be modified by reaction with C$_1$- to C$_{20}$-alcohols or ammonia or amines and be used as crosslinkers in that form.

Examples of preferred polymeric crosslinkers (7) are copolymers of acrylamide and acrylic esters, for example hydroxyethyl acrylate or methyl acrylate, the molar ratio of acrylamide and acrylic ester varying in the range from 90:10 to 10:90. Besides these copolymers, terpolymers can be used, an example of the useful combinations being acrylamide, methacrylamide and acrylates/methacrylates.

The molar mass M$_w$ of the homo- and copolymers useful as crosslinkers may for example be up to 10 000, preferably from 500 to 5000. Polymers of the abovementioned type are described for example in EP-A-0 276 464, U.S. Pat. No. 3,810,834, GB-A-1 411 063 and U.S. Pat. No. 4,818,795. The at least dibasic saturated carboxylic acids and the polycarboxylic acids may also be used as crosslinkers in the form of the alkali metal or ammonium salts. Preference is given to using the sodium salts. The polycarboxylic acids may be partially neutralized, for example to an extent of from 10 to 50 mol %, or else completely neutralized.

Useful halogen-free crosslinkers of group (8) include for example monoethylenically unsaturated monocarboxylic acids such as acrylic acid, methacrylic acid and crotonic acid and the amides, esters and anhydrides derived therefrom. The esters may be derived from alcohols of 1-22, preferably of from 1 to 18, carbon atoms. The amides are preferably unsubstituted, but may bear a C$_1$-C$_{22}$-alkyl substituent.

Preferred crosslinkers (8) are acrylic acid, methyl acrylate, ethyl acrylate, acrylamide and methacrylamide.

Useful halogen-free crosslinkers of group (9) include for example dialdehydes or their hemiacetals or acetals as precursors, for example glyoxal, methylglyoxal, malonaldehyde, succinaldehyde, malealdehyde, fumaraldehyde, tartaraldehyde, adipaldehyde, 2-hydroxyadipaldehyde, furan-2, 5-dipropionaldehyde, 2-formyl-2,3-dihydropyran, glutaraldehyde, pimelaldehyde and also aromatic dialdehydes such as, for example, terephthalaldehyde, o-phthalaldehyde, pyridine-2,6-dialdehyde or phenylglyoxal. But it is also possible to use homo- or copolymers of acrolein or methacrolein having molar masses of from 114 to about 10 000. Useful comonomers include in principle all water-soluble comonomers, for example acrylamide, vinyl acetate and acrylic acid. Aldehyde starches are similarly useful as crosslinkers.

Useful halogen-free crosslinkers of group (9) include for example diketones or the corresponding hemiketals or ketals as precursors, for example β-diketones such as acetylacetone or cycloalkane-1,n-diones such as, for example, cyclopentane-1,3-dione and cyclohexane-1,4-dione. But it is also possible to use homo- or copolymers of methyl vinyl ketone having molar masses of from 140 to about 15 000. Useful comonomers include in principle all water-soluble monomers, for example acrylamide, vinyl acetate and acrylic acid.

It will be appreciated that mixtures of two or more crosslinkers may also be used.

Preferred crosslinkers are glycidyl ethers of alkylene glycols such as ethylene glycol, propylene glycol, 1,4-butanediol, 1,6-hexanediol and polyalkylene glycols having molar masses up to 1500 and also the completely acrylated and/or methacrylated addition products of from 1 to 25 mol and preferably from 2 to 15 mol of ethylene oxide and 1 mol of trimethylolpropane or pentaerythritol.

Surfactants

The polymerizable or crosslinkable aqueous mixtures include from 0.1 to 20% by weight of at least one surfactant as a further component. The surfactants are of decisive importance for forming and stabilizing the foam. It is possible to use anionic, cationic or nonionic surfactants or surfactant mixtures which are compatible with each other. It is possible to use low molecular weight or else polymeric surfactants, and combinations of different or else similar types of surfactants have been determined to be advantageous. Examples of nonionic surfactants are addition products of alkylene oxides, especially ethylene oxide, propylene oxide and/or butylene oxide, with alcohols, amines, phenols, naphthols or carboxylic acids. The surfactants used are advantageously addition products of ethylene oxide and/or propylene oxide with alcohols containing at least 10 carbon atoms, the addition products containing from 3 to 200 mol of ethylene oxide and/or propylene oxide per mole of alcohol. The alkylene oxide units are present in the addition products in the form of blocks or in random distribution. Examples of nonionic surfactants are the addition products of 7 mol of ethylene oxide with 1 mol of tallow fat alcohol, reaction products of 9 mol of ethylene oxide with 1 mol of tallow fat alcohol and addition products of 80 mol of ethylene oxide with 1 mol of tallow fat alcohol. Further commercially available nonionic surfactants comprise reaction products of oxo process alcohols or Ziegler alcohols with from 5 to 12 mol of ethylene oxide per mole of alcohol, especially with 7 mol of ethylene oxide. Further commercially available nonionic surfactants are obtained by ethoxylation of castor oil. The amount of ethylene oxide added per mole of castor oil is for example in the range from 12 to 80 mol. Further commercially available products are for example the reaction products of 18 mol of ethylene oxide with 1 mol of tallow fat alcohol, the addition products of 10 mol of ethylene oxide with 1 mol of a $C_{13}/Cl_5$ oxo process alcohol or the reaction products of from 7 to 8 mol of ethylene oxide with 1 mol of a $C_{13}/Cl_5$ oxo process alcohol. Useful nonionic surfactants further include phenol alkoxylates such as for example p-tert-butylphenol which has been reacted with 9 mol of ethylene oxide or methyl ethers of reaction products of 1 mol of a $C_{12}$-$C_{18}$ alcohol and 7.5 mol of ethylene oxide.

The nonionic surfactants described above, for example by esterification with sulfuric acid, can be converted into the corresponding acid sulfuric esters. The acid sulfuric esters are used in the form of their alkali metal or ammonium salts as anionic surfactants. Useful anionic surfactants include for example alkali metal or ammonium salts of acid sulfuric esters of addition products of ethylene oxide and/or propylene oxide with fatty alcohols, alkali metal or ammonium salts of alkylbenzenesulfonic acid or of alkylphenol ether sulfates. Products of the kind mentioned are commercially available. For example, the sodium salt of an acid sulfuric ester of a $C_{13}/C_{15}$ oxo process alcohol reacted with 106 mol of ethylene oxide, the triethanolamine salt of dodecylbenzenesulfonic acid, the sodium salt of alkylphenol ether sulfates and the sodium salt of the acid sulfuric ester of a reaction product of 106 mol of ethylene oxide with 1 mol of tallow fat alcohol are commercially available anionic surfactants. Useful anionic surfactants further include acid sulfuric esters of $C_{13}/C_{15}$ oxo process alcohols, paraffinsulfonic acids such as $C_{15}$-alkylsulfonate, alkyl-substituted benzenesulfonic acids and alkyl-substituted naphthalenesulfonic acids such as dodecylbenzenesulfonic acid and di-n-butylnaphthalenesulfonic acid and also fatty alcohol phosphates such as $C_{15}/C_{18}$ fatty alcohol phosphate. The polymerizable aqueous mixture can include combinations of a nonionic surfactant and an anionic surfactant or combinations of nonionic surfactants or combinations of anionic surfactants. Even cationic surfactants are suitable. Examples thereof are the dimethyl sulfate quaternized reaction products of 6.5 mol of ethylene oxide with 1 mol of oleylamine, distearyldimethyl-ammonium chloride, lauryltrimethylammonium chloride, cetylpyridinium bromide and dimethyl sulfate quaternized triethanolamine stearate, which is preferably used as a cationic surfactant.

The surfactant content of the aqueous mixture is preferably in the range from 0.5 to 10% by weight. In most cases, the aqueous mixtures have a surfactant content from 1.5 to 8% by weight.

Solubilizers

The crosslinkable aqueous mixtures may optionally include at least one solubilizer as a further component. Solubilizers are water-miscible organic solvents, for example dimethyl sulfoxide, dimethylformamide, N-methylpyrrolidone, monohydric alcohols, glycols, polyethylene glycols or monoethers derived therefrom, subject to the proviso that the monoethers do not contain any double bonds in the molecule. Useful ethers include methylglycol, butylglycol, butyldiglycol, methyldiglycol, butyltriglycol, 3-ethoxy-1-propanol and glycerol monomethyl ether.

The aqueous mixtures include from 0 to 50% by weight of at least one solubilizer. When solubilizers are used, they are preferably included in the aqueous mixture in an amount from 1 to 25% by weight.

Thickeners, Foam Stabilizers, Fillers, Fibers, Cell Nucleators

The crosslinkable aqueous mixture may optionally include thickeners, foam stabilizers, fillers, fibers and/or cell nucleators. Thickeners are used for example to optimize foam structure and to improve foam stability. As a result, the foam will shrink only minimally during the polymerization. Useful thickeners include all natural and synthetic polymers known for this purpose that substantially increase the viscosity of an aqueous system and do not react with the amino groups of the basic polymers. The synthetic and natural polymers in question can be swellable or soluble in water. An exhaustive overview of thickeners may be found for example in the publications by R. Y. Lochhead and W. R. Fron, Cosmetics & Toiletries, 108, 95-135 (May 1993) and M. T. Clarke, "Rheological Additives" in D. Laba (ed.) "Rheological Properties of Cosmetics and Toiletries", Cosmetic Science and Technology Series, Vol. 13, Marcel Dekker Inc., New York 1993.

Water-swellable or water-soluble synthetic polymers useful as thickeners include for example high molecular weight polyethylene glycols or copolymers of ethylene glycol and propylene glycol and also high molecular weight polysaccharides such as starch, guar flour, locust bean flour or derivatives of natural substances such as carboxymethylcellulose, hydroxyethylcellulose, hydroxymethylcellulose, hydroxypropylcellulose and mixed cellulose ethers. A further group of thickeners are water-insoluble products, such as finely divided silica, zeolites, bentonite, cellulose powders and other finely divided powders of crosslinked polymers. The aqueous mixtures may include the thickeners in amounts up to 30% by weight. When such thickeners are used at all, they are included in the aqueous mixture in amounts of 0.1%, preferably 0.5% up to 20% by weight.

To optimize foam structure, the aqueous reaction mixture may be admixed, if applicable, with hydrocarbons having at least 5 carbon atoms in the molecule. Useful hydrocarbons include for example pentane, cyclopentane, hexane, cyclohexane, heptane, octane, isooctane, decane and dodecane. The contemplated aliphatic hydrocarbons can be straight-chain, branched or cyclic and have a boiling temperature which is above the temperature of the aqueous mixture during foaming. The aliphatic hydrocarbons extend the pot life of the foamed aqueous reaction mixture which has not yet polymerized. This facilitates the handling of the foams which have not yet polymerized and increases process consistency. The hydrocarbons act for example as cell nucleators and also stabilize the foam which has already formed. In addition, they can effect a further foaming of the mixture in the course of the polymerization of the monomer foam. They can then also have the function of a blowing agent. Instead of hydrocarbons or a mixture therewith, it is also possible to use optionally chorinated or fluorinated hydrocarbons as a cell nucleator and/or foam stabilizer, for example dichloromethane, trichloromethane, 1,2-dichloroethane, trichlorofluoromethane or 1,1,2-trichlorotrifluoroethane. When hydrocarbons are used, they are used for example in amounts from 0.1 to 20% by weight and preferably from 0.1 to 10% by weight, based on the polymerizable aqueous mixture.

To modify the properties of the foams, the crosslinkable aqueous mixture may have added to it one or more fillers, for example chalk, talc, clay, titanium dioxide, magnesium oxide, aluminum oxide, precipitated silicas in hydrophilic or hydrophobic forms, dolomite and/or calcium sulfate. The particle size of the fillers is for example in the range from 10 to 1000 μm and preferably in the range from 50 to 850 μm. Fillers can be included in the crosslinkable aqueous mixture in amounts up to 30% by weight.

The properties of the foams can optionally also be modified by means of fibers. The fibers in question can be natural or synthetic fibers or fiber blends, for example fibers composed of cellulose, wool, polyethylene, polypropylene, polyesters or polyamides. When fibers are used, they may be present in the aqueous mixture in an amount of for example up to 200% by weight and preferably up to 25% by weight. Fillers and fibers can optionally also be added to the ready-foamed mixture. The use of fibers leads to an enhancement of the strength properties, such as wet strength, of the ready-produced foam.

Water-absorbing Acidic Polymers

Useful water-absorbing acidic polymers, hereinafter also referred to as acidic superabsorbents, include all hydrogels described for example in WO-A-00/63295 page 2 line 27 to page 9 line 16. The materials in question are essentially lightly crosslinked polymers of acidic monomers that possess a high water uptake ability when in at least partially neutralized form. Examples of such crosslinked polymers, which are each lightly crosslinked, are crosslinked polyacrylic acids, crosslinked hydrolyzed graft polymers of acrylonitrile on starch, crosslinked graft polymers of acrylic acid on starch, hydrolyzed crosslinked copolymers of vinyl acetate and acrylic esters, crosslinked polyacrylamides, hydrolyzed crosslinked polyacrylamides, crosslinked copolymers of ethylene and maleic anhydride, crosslinked copolymers of isobutylene and maleic anhydride, crosslinked polyvinylsulfonic acids, crosslinked polyvinylphosphonic acids and crosslinked sulfonated polystyrene. The acidic superabsorbents mentioned can be added to the crosslinkable aqueous mixture either alone or in mixture with each other. The acidic superabsorbents used are preferably particulate polymers of neutralized polyacrylic acids which are lightly crosslinked. The acid groups of the acidic superabsorbents are preferably neutralized with aqueous sodium hydroxide solution, with sodium bicarbonate or with sodium carbonate. The neutralization can also be effected, however, with aqueous potassium hydroxide solution, ammonia, amines or alkanolamines such as ethanolamine, diethanolamine or triethanolamine.

The water-absorbing acidic polymers are added in particulate form to the crosslinkable mixture or preferably to a ready-foamed crosslinkable mixture. The particles can be used in solid form or in foamed form. The weight average particle diameter is for example in the range from 10 to 2000 μm, preferably in the range from 100 to 850 μm and usually in the range from 150 to 450 μm. Superabsorbents having the appropriate particle sizes can be prepared for example by comminution, for example by grinding, of coarsely granular, solid superabsorbents or of foamed superabsorbents. The density of the foamed acidic superabsorbents is for example in the range from 0.01 to 0.9 g/cm$^3$ and preferably in the range from 0.05 to 0.7 g/cm$^3$. The surface of the particulate superabsorbents can have been postcrosslinked, if desired. It is preferable to use acidic superabsorbents whose surface has not been postcrosslinked.

Acidic superabsorbents are known from the above-cited references, cf in particular WO-A-00/63295 page 6 line 36 to page 7 line 44. Surface postcrosslinking is effected, for example, by reacting particles of lightly crosslinked polyacrylic acids with compounds having at least two carboxyl-reactive groups. The compounds in question are typical crosslinkers which were indicated above under (b). Compounds which are of particular interest for use as crosslinkers include for example polyhydric alcohols such as propylene glycol, 1,4-butanediol or 1,6-hexanediol and glycidyl ethers of ethylene glycol and polyethylene glycols having molar masses from 200 to 1500 and preferably from 300 to 400 and completely acrylated or methacrylated reaction products of trimethylolpropane, of reaction products formed from trimethylolpropane and ethylene oxide in a molar ratio from 1:1 to 1:25 and preferably from 1:3 to 1:15 and also of reaction products of pentaerythritol with ethylene oxide in a molar ratio of 1:30 and preferably a molar ratio from 1:4 to 1:20. The postcrosslinking of the surface of the anionic superabsorbent particles is carried out for example at up to 220° C., for example preferably in the range from 120 to 190° C.

The water-absorbing acidic polymers used are superabsorbents in the form of particles having the above-indicated particle sizes. When water-absorbing acidic polymers are incorporated into the crosslinkable aqueous mixture, the polymer mixture will include for example from 10 to 90% and preferably from 30 to 70% by weight of a water-absorbing acidic polymer. The mixture of foamed basic hydrogel and the optionally foamed acidic hydrogel will usually include from 40 to 60% by weight of the acidic superabsorbent.

To prepare foams which have a high absorptive ability even for saline aqueous solutions, the basic and acidic superabsorbents are preferably used in unneutralized form. The degree of neutralization of the acidic water-absorbing polymers is for example from 0 to 100, preferably from 0 to 75 and usually from 0 to 50 mol %. The water-absorbing basic polymers have a higher uptake capacity for saline aqueous solutions and especially acidic aqueous solutions when in the form of the free bases than in acid-neutralized form. When basic polymers are used as sole water-absorbing polymers, the degree of neutralization is for example from 0 to 100 and preferably from 0 to 60 mol % %.

Superabsorbent Fiber and Fruit Fiber

According to the invention, the foam contains superabsorbent fiber which is preferably added to the aqueous polymerizable solution before foaming or to the foam. Superabsorbent fiber is known from the prior art references EP-B-0 264 208, EP-B-0 272 072, EP-B-0 436 514 and U.S. Pat. No. 4,813,945. The superabsorbent fiber is preferably fiber composed of a hydrolyzed and subsequently crosslinked copolymer of isobutene and maleic anhydride. Instead of isobutene, the copolymers may contain polymerized units derived from other 1-olefins such as ethylene, propylene, diisobutylene or styrene. The olefins mentioned and styrene are readily copolymerizable with maleic anhydride. The copolymers are hydrolyzed in an aqueous medium, neutralized with aqueous sodium or potassium hydroxide solution, for example to 20-80 mol %, mixed with crosslinkers capable of reacting with the carboxyl groups of the copolymers (eg polyhydric alcohols, polyfunctional amines or amino alcohols) and, after substantial removal of water, spun into fiber. The fiber is crosslinked by heating to for example 170-240° C., turning them into superabsorbents. Fiber diameter is for example in the range from 5 to 500 µm and preferably in the range from 10 to 300 µm, and fiber length is for example in the range from 2 to 60 mm and preferably in the range from 6 to 12 mm. The fiber is preferably added to the aqueous polymerizable mixture, but may also be added to the foamed mixture prior to curing by polymerization of the monomers or by crosslinking of the basic polymers.

As well as superabsorbent fiber it is also possible to use natural fiber. Examples of such fiber are fruit fibers such as apple fiber, orange fiber, tomato fiber, wheat fiber and/or oat fiber. Such fibers are commercially available. They are for example on offer from J. Rettenmaier & Söhne GmbH & Co., Faserstoff-Werke, D-73494 Rosenberg, under the name Vitacel®. The commercially available natural fibers of the type mentioned are reported to have the following fiber lengths:

Apple fiber <30 µm to about 1000 µm
Orange fiber <35 µm to about 1000 µm
Tomato fiber <200 µm to about 2000 µm
Wheat fiber 30 µm to 300 µm
Oat fiber 35 µm to 300 µm.

The superabsorbent fiber and the fruit fiber are used for example in amounts from 0.05 to 10% by weight and preferably from 0.1 to 5% by weight, based on the polymerizable mixture. The superabsorbent synthetic fibers have for example a Free Swell Capacity of at least 30 g/g and preferably at least 40 g/g.

Producing the Foam

The above-described crosslinkable aqueous mixtures, which contain the monomer or the basic polymer, crosslinkers, superabsorbent fiber and surfactant as mandatory components and also optionally at least one further component, are initially foamed. For example, an inert gas can be dissolved in the crosslinkable aqueous mixture at a pressure of for example 2-400 bar and the mixture subsequently decompressed to atmospheric. Decompression from a nozzle produces a flowable foam. The crosslinkable aqueous mixture can also be foamed by another method, namely by dispersing fine bubbles of an inert gas in the crosslinkable aqueous mixture. The foaming of the crosslinkable aqueous mixture on a laboratory scale can be effected for example by foaming the aqueous mixture in a kitchen processor equipped with a whisk. Foaming is preferably carried out in an inert gas atmosphere, for example in nitrogen or noble gases under atmospheric or superatmospheric pressure, for example up to 25 bar, followed by decompression. The consistency of the foams, the size of the gas bubbles and the distribution of the gas bubbles in the foam can be varied within wide limits, for example through the choice of surfactants, solubilizers, foam stabilizers, cell nucleators, thickeners and fillers. As a result, the density, the open-cell content of the foam and the wall thickness of the foam are readily adjustable to specific values. The aqueous mixture is preferably foamed at temperatures which are below the boiling point of the constituents of the aqueous mixture, for example in the range from room temperature to 100° C. and preferably in the range from 20 to 50° C. However, the aqueous mixture can also be foamed at temperatures above the boiling point of the component having the lowest boiling point by foaming the mixture in a pressuretightly sealed container. The foams obtained are crosslinkable mixtures which are flowable and stable for a prolonged period. The density of the foamed crosslinkable mixture is for example in the range from 0.01 to 0.9 g/cm$^3$ at 20° C.

Crosslinking the Foamed Mixture

The second step of the process comprises polymerization of the monomers or crosslinking the basic polymers to form a water-absorbing basic polymer. The polymerization utilizes for example crosslinkers containing two or more ethylenically unsaturated double bonds. The polymerization is conducted in the presence of customary radical-forming initiators. This gives crosslinked polymers which are superabsorbant.

The originally water-soluble polymer is rendered water-insoluble by crosslinking. A hydrogel of a basic polymer is obtained. The crosslinkable foamed mixtures are for example transferred into suitable molds and heated therein, so that the monomers polymerize and the crosslinkers react with the basic polymer. The foamed material can be applied for example in the desired thickness to a temporary carrier material which advantageously has been provided with an antistick coating. The foam can be knifecoated onto a support for example. Another possibility is to fill the aqueous foam mixture into molds which have likewise been antistick coated.

Since the foamed aqueous mixture has a long pot life, this mixture is also suitable for producing composite materials. For example, it can be applied to a permanent carrier material, for example polymeric films (films of polyethylene, polypropylene or polyamide for example) or metal such as aluminum foils. The foamed aqueous mixture can also be applied to nonwovens, fluff, tissues, wovens, natural or synthetic fibers or other foams. To prepare composite materials, it may be preferable to apply the foam in the shape of defined structures or in different layer thickness to a carrier material. However, it is also possible to apply the foam to fluff layers or nonwovens and to impregnate these materials in such a way that the fluff becomes an integral part of the foam after crosslinking. The foamed aqueous mixture obtainable in the first process step can also be molded into large blocks before crosslinking. After crosslinking, the blocks can be cut or sawed into smaller articles. It is also possible to prepare sandwichlike structures by applying a foamed aqueous mixture to a support, covering the foam layer with a film, foil, nonwoven, tissue, woven, fiber or other foam and crosslinking the sandwichlike structure by heating. However, it is also possible, before or after crosslinking, to apply at least one further layer composed of a foamed crosslinkable layer and if desired cover it with a further film, foil, nonwoven, tissue, woven, fiber or other materials. The composite is then subjected to crosslinking in the second process step. However, it is also possible to prepare sandwichlike structures having further foam layers of the same density or different densities.

Inventive foam layers having a layer thickness of up to about 1 millimeter are produced for example by heating one side or in particular by irradiating one side of the foamed polymerizable or crosslinkable aqueous mixture. When thicker layers of a foam are to be produced, for example foams having thicknesses of two or more centimeters, it is particularly advantageous to heat the crosslinkable foamed material by means of microwaves, since relatively uniform heating can be obtained in this way. In this case, the crosslinking is effected for example at from 20 to 180° C., preferably in the range from 20 to 100° C. and especially in the range from 65 to 80° C. When thicker foam layers are to be crosslinked, the foamed mixture is heat treated on both surfaces, for example using contact heating or by irradiation. The density of the basic hydrogel foams is essentially equal to the density of the crosslinkable aqueous mixture. Foams of water-absorbing basic polymers are accordingly obtained in a density of for example from 0.01 to 0.9 g/cm$^3$ and preferably from 0.1 to 0.7 g/cm$^3$. The basic polymer foams are open celled. The open-cell content is for example at least 80% and preferably above 90%. Particular preference is given to foams having an open-cell content of 100%. The open-cell content of the foam is determined using scanning electron microscopy for example.

Preference is given to foam which is obtainable when the polymerizable aqueous mixture comprises at least 50% aqueous sodium or potassium hydroxide solution neutralized acrylic acid, a crosslinker containing at least two ethylenically unsaturated double bonds, an initiator, superabsorbent fiber composed of hydrolyzed and subsequently crosslinked copolymer of isobutene and maleic anhydride, and at least one surfactant. Further examples of superabsorbent foam are obtainable when a polymerizable aqueous mixture is foamed which comprises at least one basic polymer selected from the group consisting of polymers containing vinylamine units, polymers containing vinylguanidine units, polymers containing dialkylaminoalkyl(meth)acrylamide units, polyethyleneimine, ethyleneimine-grafted polyamidoamines and polydiallyldimethylammonium chlorides.

Foams having a particularly high water uptake capacity and an improved uptake ability for electrolyte-containing aqueous solutions are obtainable by crosslinking foamed aqueous mixtures of basic polymers which, based on the polymer mixture, include from 10 to 90% by weight of a finely divided water-absorbing acidic polymer. The acidic hydrogel can be present in the foams of the invention as a solid particulate polymer or as a foamed particulate polymer having particle sizes of for example 10-2000 μm.

After the crosslinking of the foamed mixture or during the crosslinking, the hydrogel foam is dried. This removes water and other volatile constituents from the crosslinked hydrogel foam. Preferably, the hydrogel foam is dried after it has been crosslinked. Examples of suitable drying processes are thermal convection drying, for example tray, chamber, duct, flat sheet, disk, rotary drum, free fall tower, foraminous belt, flow, fluidized bed, moving bed, paddle and ball bed drying, thermal contact drying such as hotplate, drum, belt, foraminous cylinder, screw, tumble and contact disk drying, radiative drying such as infrared drying, dielectric drying such as microwave drying and freeze drying. To avoid unwelcome decomposition and crosslinking reactions, it may be advantageous to dry under reduced pressure, under a protective gas atmosphere and/or under benign thermal conditions where the product temperature does not exceed 120° C., preferably 100° C. Particularly suitable drying processes are (vacuum) belt drying and paddle drying.

After drying, the hydrogel foam will usually no longer contain any water. However, the water content of the foamed material can be adjusted to any desired value by moistening the foam with liquid water or water vapor. The water content of the gel foam is usually in the range from 1 to 60% by weight and preferably in the range from 2 to 10% by weight. The water content can be used to adjust the flexibility of the hydrogel foam. Completely dried hydrogel foams are rigid and brittle, whereas foamed materials having a water content of for example 5-20% by weight are flexible. The foamed hydrogels can either be used directly in the form of sheets or granules or cut into individual plates or sheets from thicker blocks.

However, the hydrogel foams described above can additionally be modified to the effect that the surface of the foamed materials is postcrosslinked. This is a way of improving the gel stability of the articles formed from the foamed hydrogels. To perform surface postcrosslinking, the surface of the articles formed from the foamed hydrogels is treated with at least one crosslinking agent and the thus treated articles are heated to a temperature at which the crosslinkers will react with the hydrogels. Suitable crosslinkers are described above. These compounds can likewise be used for postcrosslinking the surface of the hydrogel foams.

Crosslinkers which are preferably used are the hereinabove mentioned glycidyl ethers and esters of acrylic acid and/or methacrylic acid with the reaction products of 1 mol of trimethylolpropane and from 6 to 15 mol of ethylene oxide or polyhydric alcohols which are used for example to postcrosslink carboxyl-containing superabsorbent foams.

The crosslinkers for the surface postcrosslinking are preferably applied to the foam surface in the form of an aqueous solution. The aqueous solution can include water-miscible organic solvents, for example alcohols such as methanol, ethanol and/or i-propanol or ketones such as acetone. The amount of crosslinker applied to the surface of the hydrogel foams is for example in the range from 0.1 to 5% by weight and preferably in the range from 1 to 2% by weight. The surface postcrosslinking of the hydrogel foams is effected by heating the hydrogel foams which have been treated with at least one crosslinker to a temperature which is for example in the range from 60 to 120° C. and preferably in the range from 70 to 100° C. After surface crosslinking, the water content of the foamed surface-postcrosslinked hydrogel can likewise be adjusted to values from 1 to 60% by weight.

The optionally surface-postcrosslinked hydrogel foams of the invention can be used for all the purposes for which for example the water-absorbing hydrogel foams which are known from EP-B-0 858 478 and which are based on acid group containing polymers such as crosslinked polyacrylates are used. The hydrogel foams of the invention are useful for example in hygiene articles to absorb body fluids, in dressing material to cover wounds, as a sealing material, as a packaging material, as a soil improver, as a soil substitute, to dewater sludges, to absorb aqueous acidic wastes, to thicken waterborne paints or coatings in the course of disposing of residual quantities thereof, to dewater water-containing oils or hydrocarbons or as a material for filters in ventilation systems.

Of particular importance is the use of the hydrogel foams of the invention in hygiene articles, such as baby diapers, sanitary napkins and incontinence articles, and in dressing material. In hygiene articles for example they perform more than one function, namely acquire, distribute and/or store body fluids. The surface of the hydrogel foams can optionally be modified by treatment with surfactants or polymers containing uncrosslinked vinylamine units. This provides an improvement in the acquisition of fluids.

Layers of the hydrogel foams according to the invention can be for example disposed in a thickness from 1 to 5 mm in one of the abovementioned hygiene articles as an absorbent core between a liquid-pervious topsheet and a liquid-impervious layer composed of a film of for example polyethylene or polypropylene. The liquid-pervious layer of the hygiene article is in direct contact with the skin of the user. This material is customarily composed of a nonwoven of natural fibers such as cellulose fibers or fluff. If desired, a tissue layer will be disposed above and/or below the absorbent core. Between the bottom layer of the hygiene article and the absorbent core, there may optionally be a storage layer composed of a conventional particulate anionic superabsorbent. When the foamed basic hydrogels are used as an absorbent core in diapers, the open-cell structure of the foamed basic hydrogel will ensure that the body fluid, which is normally applied in individual amounts all at once, is speedily removed. This gives the user a pleasant sense of the surface dryness of the diaper.

Methods of Determination

Density

Any suitable gravimetric method can be used for determining the density of the multicomponent foam system. What is determined is the mass of solid multicomponent foam system per unit volume of foam structure. A method for density determination of the multicomponent foam system is described in ASTM Method No. D 3574-86, Test A. This method was originally developed for the density determination of urethane foams, but can also be used for this purpose. By this method, the dry mass and volume of a preconditioned sample is determined at 22+/−2° C. Volume determination of larger sample dimensions are carried out under atmospheric pressure.

Free Swell Capacity (FSC)

This method is used to determine the free swellability of the multicomponent foam system in a teabag. To determine FSC, 0.2000±0.0050 g of dried foam is introduced into a teabag 60×85 mm in size, which is subsequently sealed shut. The teabag is placed in an excess of test solution (at least 0.83 l of sodium chloride solution/1 g of polymer) for 30 minutes. The teabag is subsequently allowed to drip for 10 minutes by being hung up by one corner. The amount of liquid is determined by weighing back the teabag.

The test solution used was 0.9% by weight NaCl solution.

Centrifuge Retention Capacity (CRC)

This method is used to determine the free swellability of the multicomponent foam system in a teabag. To determine CRC, 0.2000±0.0050 g of dried multicomponent foam is introduced into a teabag 60×85 mm in size, which is subsequently sealed shut. The teabag is placed in an excess of 0.9% by weight sodium chloride solution (at least 0.83 l of sodium chloride solution/1 g of polymer) for 30 minutes. The teabag is then centrifuged at 250 G for 3 minutes. The amount of liquid is determined by weighing back the centrifuged teabag.

The test solution used was 0.9% by weight NaCl solution

Free Swell Rate (FSR)

To determine the free swell rate, 0.50 g ($W_H$) of the multicomponent foam system is placed on the base of a plastic dish having a round bottom of about 6 cm. The plastic dish is about 2.5 cm deep and has a square opening of about 7.5 cm×7.5 cm. A funnel is then used to add 10 g ($W_U$) of a 0.9% NaCl solution into the center of the plastic dish. As soon as the liquid has contact with the multicomponent foam system, time measurement is started and not stopped until the multicomponent foam system has completely taken up the entire liquid, ie until pooled liquid is absent. This time is noted as $t_A$. The free swell rate then computes from $$FSR = W_U/(W_H \times t_A).$$

K value

The K value was determined after H. Fikentscher, Cellulose-Chemie, Volume 13, 52-63 and 71-74 (1932) in 5% by weight aqueous solution at pH 7, 25° C. and a polymer concentration of 0.5% by weight.

Wet Failure Value (WFV) of Superabsorbent Foam

The Wet Failure Value is the force needed to destroy a test specimen of a fully swollen superabsorbent foam under controlled conditions in the hereinbelow described apparatus. The superabsorbent foam is swollen in synthetic urine or in 0.9% by weight aqueous sodium chloride solution until it ceases to take up liquid.

Figure 2:
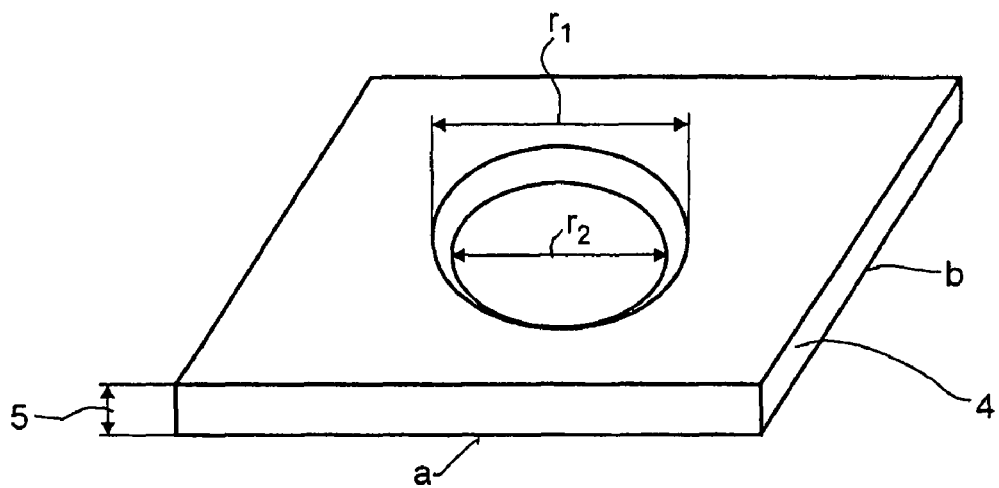
Figure 3:
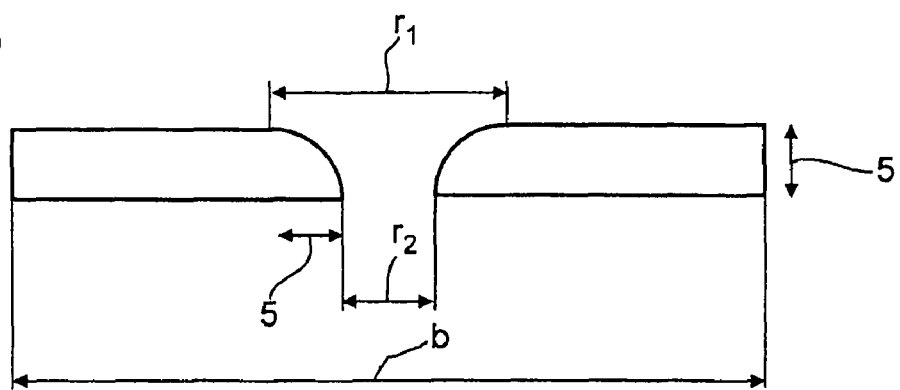
FIG. 3 is a side view of a metal plate used in the instrument for measuring the WFV of a superabsorbent foam.

The Wet Failure Value is measured in a commercially available texture analyzer (TA-XT2) from Stable Micro Systems, Surrey, UK. The measuring instrument is diagrammed in FIG. 1. A measuring arm (1) has attached to it a sphere (2) of stainless steel 1 inch (2.54 cm) in diameter that can be brought to bear on a sample of the swollen superabsorbent foam (3) held between two metal plates. Both the metal plates have a hole in the middle that has a diameter r1=5.1 cm and a diameter r2=3.5 cm, cf FIG. 2. As is revealed by FIG. 3, the side of the plate with the r1 diameter has a rounded shape which corresponds to a quarter segment of a circle having a diameter of 0.8 cm. Only this side of each plate comes into contact with the superabsorbent foam to be analyzed. The rounded shape—cf FIG. 3—is important in order that the foam being analyzed is not damaged by sharp-edged corners in the course of testing. The place surfaces which come into contact with the foam are roughened in order that the foam may be held in place during testing.

The plates each are 0.8 cm thick and have edge lengths a=10 cm and b=9 cm. The foam sample is located between the two plates as indicated above. The instrument is set to a load of 5000 g. To determine the wet failure value, the sphere (2) connected to the measuring arm (1) is then lowered at a speed of 0.5 mm/s and the force needed to destroy the foam sample is measured. The maximum distance which the sphere (2) travels in the course of measurement is 30 mm. The sphere pushes through the foam situated between the two plates. The requisite force per unit area is determined and reported as WFV in $g/mm^2$.

Three samples are prepared of each foam and measured as described above. It is important here that the foam samples to be analyzed do not contain holes or comparatively large air inclusions, since they would falsify the measurements.

Determination of Thickness of Swollen Foam

The thickness of the swollen foam was determined by means of a Digimatic thickness gauge from Mitutoyo. The thickness of the foam was measured as soon as it was fully swollen.

Cross Sectional Area (CSA)

The area of the cross section is determined on the fully swollen foam by considering only that area which is obtained from the diameter (r2=35 mm) and the thickness of the swollen foam in the equilibrium state (Te) by the following formular:

$$CSA[mm^2] = 35 \times Te$$

Wet Failure Point is the maximum force (F) [g] which is indicated in the texture analyzer by the peak maximum and which is needed to destroy the fully swollen foam sample in the texture analyzer of FIG. 1.

Wet Failure Value (WFV)

is obtained from the maximum force (F) needed to destroy the swollen foam sample and the Cross Sectional Area of the fully swollen foam as per $$WFV[g/mm^2] = \text{maximum force}/CSA$$

Superabsorbent Fiber

The Fiberdri® superabsorbent fiber from Camelot Technologies Limited, Canada, that is used in the examples is based on crosslinked hydrolyzed copolymers of isobutene and maleic anhydride after partial neutralization with aqueous sodium hydroxide solution.

The OASIS® superabsorbent fiber from Technical Absorbents Limited, UK, also used in the examples are based on crosslinked copolymers of sodium acrylate, hydroxypropyl acrylate and methyl acrylate.

Unless suggested otherwise by the context, the percentages in the examples are by weight.

Preparation of an Acidic Particulate Water-absorbing Polymer (SAP 1)

270 g of acrylic acid were weighed into a beaker. 1.155 g of methylenebisacrylamide (MBA) crosslinker were then added, the monomers were stirred until everything had dissolved. 810 g of distilled water were weighed into a separate vessel and added to the monomer mixture. The solution was stirred to complete the mixture. The aqueous monomer solution was subsequently stored in a freezer cabinet for cooling for about 1 hour.

A 10% sodium persulfate solution was prepared with distilled water and added to a cooled polymerization tank. 0.157 g of 2-hydroxy-2-methyl-1-phenylpropan-1-one (Darocur® 1173, Ciba, photoinitiator) and 2.736 g of the 10% sodium persulfate solution were added as initiator system. A final mixing step provided the homogenous system which was left until it had attained a temperature of 10° C., at which the polymerization reaction was then carried out within 12 minutes by irradiating with a UV dose of 20 mWcm$^{-2}$. This provided a gellike addition polymer, which was comminuted and fully dried at 125° C. The dried addition polymer obtained was ground and the fraction having an average particle size of 150 μm-450 μm was sieved off.

EXAMPLES

Inventive Example 1

The following components were mixed in a beaker by means of a magnetic stirrer:

| | |
|---|---|
| 348.55 g | of acrylic acid (4.84 mol) |
| 135.51 g | of a 37.3% sodium acrylate solution in water (0.54 mol) |
| 28 g | of an ethoxylated trimethylolpropane triacrylate of molar mass 956 (ETMPTA) |
| 21.33 g | of a 15% aqueous solution of an addition product of 80 mol of ethylene oxide to 1 mol of a linear saturated $C_{16}C_{18}$ fatty alcohol |
| 65.70 g | of water |

To this solution were added with ice cooling 400.90 g (2.69 mol) of triethanolamine such that the internal temperature did not rise above 16° C. To the aqueous mixture was then added 0.5% by weight on monomers (2.4 g) of superabsorbent fiber (Fiberdri P8/00 1231, ex Camelot Technologies Limited, Canada). The solution obtained was transferred into a pressure vessel and saturated therein with carbon dioxide at 12 bar for 25 min. 26.67 g of a 3% aqueous solution of 2,2'-azobis (2-amidinopropane) dihydrochloride were added under pressure and homogeneously mixed in by raising the pressure. This was followed by passing carbon dioxide through the reaction mixture for a further 5 min. The saturated reaction mixture was expressed at 12 bar through a die 1 mm in diameter to form a free-flowing fine-cell foam.

The monomer foam obtained was applied to an A3-size glass plate having rims 3 mm high and was covered with a second glass plate. The foam sample was irradiated simultaneously from both sides with two UV/VIS radiators (UV 1000 from Höhnle) for 4 minutes.

The foam layer obtained was fully dried in a vacuum drying cabinet at 70° C. and subsequently adjusted to a moisture content of 5% by spraying with water.

| | |
|---|---|
| Solids content of reaction mixture: | 81.74% |
| Degree of neutralization: | 60 mol % |
| Monomer foam density: | 0.24 gcm$^{-3}$ |
| Polymer foam density: | 0.20 gcm$^{-3}$ |
| Foam structure: | homogeneous, fully open-cell, no skin |

Further properties of the open-cell foam are reported in Tables 1 and 2.

Inventive Example 2

The following components were mixed in a beaker by means of a magnetic stirrer.

| | |
|---|---|
| 348.55 g | of acrylic acid (4.84 mol) |
| 135.51 g | of a 37.3% sodium acrylate solution in water (0.54 mol) |
| 28 g | of an ethoxylated trimethylolpropane triacrylate of molar mass 956 (ETMPTA) |
| 21.33 g | of a 15% aqueous solution of an addition product of 80 mol of ethylene oxide to 1 mol of a linear saturated $C_{16}C_{18}$ fatty alcohol |
| 65.70 g | of water |

To this solution were added with ice cooling 400.90 g (2.69 mol) of triethanolamine such that the internal temperature did not rise above 16° C. To the aqueous mixture was then added 1.0% by weight on monomers (4.8 g) of superabsorbent fiber (Fiberdri P8/00 1231, ex Camelot Technologies Limited, Canada). The solution obtained was transferred into a pressure vessel and saturated therein with carbon dioxide at 12 bar for 25 min. 26.67 g of a 3% aqueous solution of 2,2'-azobis (2-amidinopropane) dihydrochloride were added under pressure and homogeneously mixed in by raising the pressure. This was followed by passing carbon dioxide through the reaction mixture for a further 5 min. The saturated reaction mixture was expressed at 12 bar through a die 1 mm in diameter to form a free-flowing fine-cell foam.

The monomer foam obtained was applied to an A3-size glass plate having rims 3 mm high and was covered with a second glass plate. The foam sample was irradiated simultaneously from both sides with two UV/VIS radiators (UV 1000 from Höhnle) for 4 minutes.

The foam layer obtained was fully dried in a vacuum drying cabinet at 70° C. and subsequently adjusted to a moisture content of 5% by spraying with water.

| | |
|---|---|
| Solids content of reaction mixture: | 82.13% |
| Degree of neutralization: | 60 mol % |
| Monomer foam density: | 0.28 gcm$^{-3}$ |
| Polymer foam density: | 0.22 gcm$^{-3}$ |
| Foam structure: | homogeneous, fully open-cell, no skin |

Further properties of the open-cell foam are reported in Tables 1 and 2.

Inventive Example 3

The following components were mixed in a beaker by means of a magnetic stirrer.

| | |
|---|---|
| 348.55 g | of acrylic acid (4.84 mol) |
| 135.51 g | of a 37.3% sodium acrylate solution in water (0.54 mol) |
| 28 g | of an ethoxylated trimethylolpropane triacrylate of molar mass 956 (ETMPTA) |
| 21.33 g | of a 15% aqueous solution of an addition product of 80 mol of ethylene oxide to 1 mol of a linear saturated $C_{16}C_{18}$ fatty alcohol |
| 65.70 g | of water |

To this solution were added with ice cooling 400.90 g (2.69 mol) of triethanolamine such that the internal temperature did not rise above 16° C. To the aqueous mixture was then added 3% by weight on monomers (14.40 g) of superabsorbent fiber (Fiberdri P8/00 1231, ex Camelot Technologies Limited, Canada). The solution obtained was transferred into a pressure vessel and saturated therein with carbon dioxide at 12 bar for 25 min. 26.67 g of a 3% aqueous solution of 2,2'-azobis (2-amidinopropane) dihydrochloride were added under pressure and homogeneously mixed in by raising the pressure. This was followed by passing carbon dioxide through the reaction mixture for a further 5 min. The saturated reaction mixture was expressed at 12 bar through a die 1 mm in diameter to form a free-flowing fine-cell foam.

The monomer foam obtained was applied to an A3-size glass plate having rims 3 mm high and was covered with a second glass plate. The foam sample was irradiated simultaneously from both sides with two UV/VIS radiations (UV 1000 from Höhnle) for 4 minutes.

The foam layer obtained was fully dried in a vacuum drying cabinet at 70° C. and subsequently adjusted to a moisture content of 5% by spraying with water.

| | |
|---|---|
| Solids content of reaction mixture: | 81.99% |
| Degree of neutralization: | 60 mol % |
| Monomer foam density: | 0.26 gcm$^{-3}$ |
| Polymer foam density: | 0.21 gcm$^{-3}$ |
| Foam structure: | homogeneous fully open cell, no skin |

Further properties of the open-cell foam are reported in Tables 1 and 2.

Inventive Example 4

The following components were mixed in a beaker by means of a magnetic stirrer.

| | |
|---|---|
| 348.55 g | of acrylic acid (4.84 mol) |
| 135.51 g | of a 37.3% sodium acrylate solution in water (0.54 mol) |
| 28 g | of an ethoxylated trimethylolpropane triacrylate of molar mass 956 (ETMPTA) |
| 21.33 g | of a 15% aqueous solution of an addition product of 80 mol of ethylene oxide to 1 mol of a linear saturated $C_{16}C_{18}$ fatty alcohol |
| 65.70 g | of water |

To this solution were added with ice cooling 400.90 g (2.69 mol) of triethanolamine such that the internal temperature did not rise above 16° C. To the aqueous mixture was then added 0.1% by weight on monomers (0.48 g) of superabsorbent fiber (Fiberdri P8/00 1231, ex Camelot Technologies Limited, Canada). The solution obtained was transferred into a pressure vessel and saturated therein with carbon dioxide at 12 bar for 25 min. 26.67 g of a 3% aqueous solution of 2,2'-azobis(2-amidinopropane) dihydrochloride were added under pressure and homogeneously mixed in by raising the pressure. This was followed by passing carbon dioxide through the reaction mixture for a further 5 min. The saturated reaction mixture was expressed at 12 bar through a die 1 mm in diameter to form a free-flowing fine-cell foam.

The monomer foam obtained was applied to an A3-size glass plate having rims 3 mm high and was covered with a second glass plate. The foam sample was irradiated simultaneously from both sides with two UV/VIS radiators (UV 1000 from Höhnle) for 4 minutes.

The foam layer obtained was fully dried in a vacuum drying cabinet at 70° C. and subsequently adjusted to a moisture content of 5% by spraying with water.

| | |
|---|---|
| Solids content of reaction mixture: | 81.43% |
| Degree of neutralization: | 60 mol % |
| Monomer foam density: | 0.21 gcm$^{-3}$ |
| Polymer foam density: | 0.19 gcm$^{-3}$ |
| Foam structure: | homogeneous fully open cell, no skin |

Further properties of the open-cell foam are reported in Tables 1 and 2.

Invention Example 5

The following components were mixed in a beaker by means of a magnetic stirrer.

| | |
|---|---|
| 348.55 g | of acrylic acid (4.84 mol) |
| 135.51 g | of a 37.3% sodium acrylate solution in water (0.54 mol) |
| 28 g | of polyethylene glycol diacrylate of a polyethylene glycol of molar mass 400 |
| 21.33 g | of a 15% aqueous solution of an addition product of 80 mol of ethylene oxide to 1 mol of a linear saturated $C_{16}C_{18}$ fatty alcohol |
| 65.70 g | of water |

To this solution were added with ice cooling 400.90 g (2.69 mol) of triethanolamine such that the internal temperature did not rise above 16° C. To the aqueous mixture was then added 1.0% by weight on monomers (4.8 g) of superabsorbent fiber (Fiberdri P8/00 1231, ex Camelot Technologies Limited, Canada). The solution obtained was transferred into a pressure vessel and saturated therein with carbon dioxide at 12 bar for 25 min. 26.67 g of a 3% aqueous solution of 2,2'-azobis (2-amidinopropane) dihydrochloride were added under pressure and homogeneously mixed in by raising the pressure. This was followed by passing carbon dioxide through the reaction mixture for a further 5 min. The saturated reaction mixture was expressed at 12 bar through a die 1 mm in diameter to form a free-flowing fine-cell foam.

The monomer foam obtained was applied to an A3-size glass plate having rims 3 mm high and was covered with a second glass plate. The foam sample was irradiated simultaneously from both sides with two UV/VIS radiators (UV 1000 from Höhnle) for 4 minutes.

The foam layer obtained was fully dried in a vacuum drying cabinet at 70° C. and subsequently adjusted to a moisture content of 5% by spraying with water.

| Solids content of reaction mixture: | 82.13% |
| Degree of neutralization: | 60 mol % |
| Monomer foam density: | 0.23 gcm$^{-3}$ |
| Polymer foam density: | 0.20 gcm$^{-3}$ |
| Foam structure: | homogeneous fully open-cell, no skin |

Further properties of the open-cell foam are reported in Tables 1 and 2.

Inventive Example 6

The following components were mixed in a beaker by means of a magnetic stirrer.

| 348.55 g | of acrylic acid (4.84 mol) |
| 135.51 g | of a 37.3% sodium acrylate solution in water (0.54 mol) |
| 28 g | of an ethoxylated trimethylolpropane triacrylate of molar mass 956 (ETMPTA) |
| 21.33 g | of a 15% aqueous solution of an addition product of 80 mol of ethylene oxide to 1 mol of a linear saturated $C_{16}C_{18}$ fatty alcohol |
| 65.70 g | of water |

To this solution were added with ice cooling 400.90 g (2.69 mol) of triethanolamine such that the internal temperature did not rise above 16° C. To the aqueous mixture was then added 1% by weight on monomers (0.48 g) of superabsorbent fiber (OASIS® ex Technical Absorbents Limited, UK). The solution obtained was transferred into a pressure vessel and saturated therein with carbon dioxide at 12 bar for 25 min. 26.67 g of a 3% aqueous solution of 2,2'-azobis(2-amidinopropane) dihydrochloride were added under pressure and homogeneously mixed in by raising the pressure. This was followed by passing carbon dioxide through the reaction mixture for a further 5 min. The saturated reaction mixture was expressed at 12 bar through a die 1 mm in diameter to form a free-flowing fine-cell foam.

The monomer foam obtained was applied to an A3-size glass plate having rims 3 mm high and was covered with a second glass plate. The foam sample was irradiated simultaneously from both sides with two UV/VIS radiators (UV 1000 from Höhnle) for 4 minutes.

The foam layer obtained was fully dried in a vacuum drying cabinet at 70° C. and subsequently adjusted to a moisture content of 5% by spraying with water.

| Solids content of reaction mixture: | 82.13% |
| Degree of neutralization: | 60 mol % |
| Monomer foam density: | 0.33 gcm$^{-3}$ |
| Polymer foam density: | 0.29 gcm$^{-3}$ |
| Foam structure: | homogeneous fully open-cell, no skin |

Further properties of the open-cell foam are reported in Tables 1 and 2.

Inventive Example 7

To 300 g of a 10% ultrafiltered aqueous solution of polyvinylamine (PVAm) having a K value of 90 were added 15 g of a 5% aqueous solution of a commercially available surfactant (addition product of 80 mol of ethylene oxide with 1 mol of C16/C18 alcohol mixture) and 15 g of a 5% aqueous solution of ethylene glycol diglycidyl ether crosslinker.

The crosslinkable mixture was then foamed in the shearing zone of an Ultraturrax stirrer for 1 minute. To samples of the crosslinkable aqueous mixture were then added 1% by weight (0.3 g), based on PVAm, of a superabsorbent fiber (Fiberdri P8/00 1231, ex Camelot Technologies Limited, Canada). The mixture was then stirred for 1 minute. This gave a homogeneous mixture. The foamed crosslinkable mixtures thus prepared were each poured onto a Teflon support rimmed with aluminum. The mold containing the foamed crosslinkable mixture was stored at 70° C. in a drying cabinet overnight. The hydrogel foam obtained was subsequently adjusted to a water content of 5%.

| Solids content of reaction mixture: | 10% |
| Degree of neutralization: | 0 mol % |
| Polymer foam density: | 0.18 gcm$^{-3}$ |
| Foam structure: | homogeneous, fully open-cell |

Further properties of the open-cell foam are reported in Tables 1 and 2.

Inventive Example 8

To 300 g of a 10% ultrafiltered aqueous solution of polyvinylamine having a K value of 90 were added 15 g of a 5% aqueous solution of a commercially available surfactant (addition product of 80 mol of ethylene oxide with 1 mol of $C16/C_{1-8}$ alcohol mixture) and 15 g of a 5% aqueous solution of ethylene glycol diglycidyl ether crosslinker.

The crosslinkable mixture was then foamed in the shearing zone of an Ultraturrax stirrer for 1 minute. To samples of the crosslinkable aqueous mixture were added first 45 g of SAP 1 and then 1% by weight (0.3 g), based on PVAm, of a superabsorbent fiber (Fiberdri P8/00 1231, ex Camelot Technologies Limited, Canada). The mixture was then stirred for 1 minute. This gave a homogeneous mixture. The foamed crosslinkable mixtures thus prepared were each poured onto a Teflon support rimmed with aluminum. The mold containing the foamed crosslinkable mixture was stored at 70° C. in a drying cabinet overnight. The hydrogel foam obtained was subsequently adjusted to a water content of 5%.

| | |
|---|---|
| Solids content of reaction mixture: | 22.5% |
| Polymer foam density: | 0.20 gcm$^{-3}$ |
| Foam structure: | homogeneous, fully open-cell |

Further properties of the open-cell foam are reported in Tables 1 and 2.

Comparative Example 1

Comparison as per Example 1 of WO-A-00/52087

The following components were mixed in a beaker by means of a magnetic stirrer:

| | |
|---|---|
| 348.55 g | of acrylic acid (4.84 mol) |
| 135.51 g | of a 37.3% sodium acrylate solution in water (0.54 mol) |
| 28 g | of polyethylene glycol diacrylate of a polyethylene glycol of molar mass 400 |
| 21.33 g | of a 15% aqueous solution of an addition product of 80 mol of ethylene oxide to 1 mol of a linear saturated $C_{16}C_{18}$ fatty alcohol |
| 65.70 g | of water |

To this solution were added with ice cooling 400.90 g (2.69 mol) of triethanolamine such that the internal temperature did not rise above 16° C. The solution obtained was transferred into a pressure vessel and saturated therein with carbon dioxide at 12 bar for 25 min. 26.67 g of a 3% aqueous solution of 2,2'-azobis(2-amidinopropane) dihydrochloride were added under pressure and homogeneously mixed in by raising the pressure. This was followed by passing carbon dioxide through the reaction mixture for a further 5 min. The saturated reaction mixture was expressed at 12 bar through a die 1 mm in diameter to form a free-flowing fine-cell foam.

The monomer foam obtained was applied to an A3-size glass plate having rims 3 mm high and was covered with a second glass plate.

The foam sample was irradiated simultaneously from both sides with two UV/VIS radiators (UV 1000 from Höhnle) for 4 minutes.

The foam layer obtained was fully dried in a vacuum drying cabinet at 70° C. and subsequently adjusted to a moisture content of 5% by spraying with water.

| | |
|---|---|
| Solids content of reaction mixture: | 81.04% |
| Degree of neutralization: | 60 mol % |
| Monomer foam density: | 0.21 gcm$^{-3}$ |
| Polymer foam density: | 0.20 gcm$^{-3}$ |
| Foam structure: | homogeneous, fully open-cell, no skin |

Further properties of the open-cell foam are reported in Tables 1 and 2.

TABLE 1

| Example | FSC [g/g] | CRC [g/g] | FSR [g/gsec] |
|---|---|---|---|
| Inventive 1 | 50.3 | 11.0 | 4.9 |
| Inventive 2 | 48.2 | 10.9 | 4.6 |
| Inventive 3 | 44.4 | 11.2 | 4.2 |
| Inventive 4 | 50.0 | 10.4 | 5.5 |

TABLE 1-continued

| Example | FSC [g/g] | CRC [g/g] | FSR [g/gsec] |
|---|---|---|---|
| Inventive 5 | 50.5 | 8.3 | 7.9 |
| Inventive 6 | 36.0 | 10.8 | 2.9 |
| Inventive 7 | 41.7 | 12.3 | 1.9 |
| Inventive 8 | 38.5 | 19.4 | 0.2 |
| Comparative 1 | 56.6 | 7.7 | 4.4 |

TABLE 2

| Example | Swollen foam thickness [mm] | CSA [mm$^2$] | Wet Failure Point [g] | WFV [g/mm$^2$] |
|---|---|---|---|---|
| Inventive 1 | 5.41 | 189.3 | 47.0 | 0.269 |
| Inventive 2 | 6.03 | 211.1 | 60.3 | 0.340 |
| Inventive 3 | 6.48 | 226.8 | 44.2 | 0.234 |
| Inventive 4 | 7.80 | 273.0 | 66.8 | 0.245 |
| Inventive 5 | 9.46 | 331.1 | 50.4 | 0.152 |
| Inventive 6 | 8.38 | 293.3 | 90.8 | 0.310 |
| Inventive 7 | 8.70 | 304.5 | 262.3 | 1.315 |
| Inventive 8 | 10.09 | 353.2 | 158.5 | 0.423 |
| Comparative 1 | 12.60 | 441.0 | 41.0 | 0.093 |

Inventive Example 9

The following components were mixed in a beaker by means of a magnetic stirrer.

| | |
|---|---|
| 348.55 g | of acrylic acid (4.84 mol) |
| 135.51 g | of a 37.3% sodium acrylate solution in water (0.54 mol) |
| 28 g | of an ethoxylated trimethylolpropane triacrylate of molar mass 956 (ETMPTA) |
| 21.33 g | of a 15% aqueous solution of an addition product of 80 mol of ethylene oxide to 1 mol of a linear saturated $C_{16}C_{18}$ fatty alcohol |
| 65.70 g | of water |

To this solution were added with ice cooling 400.90 g (2.69 mol) of triethanolamine such that the internal temperature did not rise above 16° C. The solution obtained was transferred into a pressure vessel and saturated therein with carbon dioxide at 12 bar for 25 min. 26.67 g of a 3% aqueous solution of 2,2'-azobis(2-amidinopropane) dihydrochloride were added under pressure and homogeneously mixed in by raising the pressure. This was followed by passing carbon dioxide through the reaction mixture for a further 5 min. The saturated reaction mixture was expressed at 12 bar through a die 1 mm in diameter to form a free-flowing fine-cell foam.

Into a mold, an A4-size glass plate having rims 1 mm high, was placed a 0.69 mm thick nonwoven web of superabsorbent (Fiberdri P8/00 1231, ex Camelot Technologies Limited, Canada) having a web density of 0.0995 g/cm$^3$ and the previously prepared monomer foam was then applied to the web and carefully worked into the web while keeping the open-cell foam structure intact. The mold was then covered with a second glass plate. The foam sample was then polymerized between the two glass plates by irradiating the glass plates simultaneously from both sides with two UV/VIS radiators (UV 1000 from Höhnle) for 4 minutes.

The foam layer obtained was fully dried in a vacuum drying cabinet at 70° C. and subsequently adjusted to a moisture content of 5% by spraying with water.

| | |
|---|---|
| Solids content of reaction mixture: | 81.35% |
| Degree of neutralization: | 60 mol % |
| Monomer foam density: | 0.22 gcm$^{-3}$ |
| Polymer foam density with web: | 0.29 gcm$^{-3}$ |
| Foam structure: | homogeneous, fuly open-cell, no skin |
| Foam and web: | 458 g/m$^2$ |

Further properties of the open-cell foam are reported in Table 3.

TABLE 3

| Example | Dry foam thickness [mm] | Swollen foam thickness [mm] | CSA [mm$^2$] | Wet failure point [g] | WFV [g/mm$^2$] |
|---|---|---|---|---|---|
| Inv. 9 | 1.75 | 3.25 | 113.75 | 25.7 | 0.226 |

Inventive Example 10

The following components were mixed in a beaker by means of a magnetic stirrer.

| | |
|---|---|
| 348.55 g | of acrylic acid (4.84 mol) |
| 135.51 g | of a 37.3% sodium acrylate solution in water (0.54 mol) |
| 28 g | of an ethoxylated trimethylolpropane triacrylate of molar mass 956 (ETMPTA) |
| 21.33 g | of a 15% aqueous solution in an addition product of 80 mol of ethylene oxide to 1 mol of a linear saturated C$_{16}$C$_{18}$ fatty alcohol |
| 65.70 g | of water |

To this solution were added with ice cooling 400.90 g (2.69 mol) of triethanolamine such that the internal temperature did not rise above 16° C. To the aqueous mixture was then added 1.0% by weight (4.8 g), based on monomers, of apple fiber (Bio-Apfelfaser AF 400, ex J. Rettenmaier & Söhne GmbH & Co, Germany). The solution obtained was transferred into a pressure vessel and saturated therein with carbon dioxide at 12 bar for 25 min. 26.67 g of a 3% aqueous solution of 2,2'-azobis(2-amidinopropane) dihydrochloride were added under pressure and homogeneously mixed in by raising the pressure. This was followed by passing carbon dioxide through the reaction mixture for a further 5 min. The saturated reaction mixture was expressed at 12 bar through a die 1 mm in diameter to form a free-flowing fine-cell foam.

The monomer foam obtained was applied to an A3-size glass plate having rims 3 mm high and was covered with a second glass plate. The foam sample was irradiated simultaneously from both sides with two UV/VIS radiators (UV 1000 from Höhnle) for 4 minutes.

The foam layer obtained was fully dried in a vacuum drying cabinet at 70° C. and subsequently adjusted to a moisture content of 5% by spraying with water.

| | |
|---|---|
| Solids content of reaction mixture: | 82.13% |
| Degree of neutralization: | 60 mol % |
| Monomer foam density: | 0.25 gcm$^{-3}$ |
| Polymer foam density: | 0.27 gcm$^{-3}$ |
| Foam structure: | homogeneous, fully open-cell, no skin |

Further properties of the open-cell foam are reported in Tables 4 and 5.

Inventive Example 11

The following components were mixed in a beaker by means of a magnetic stirrer.

| | |
|---|---|
| 348.55 g | of acrylic acid (4.84 mol) |
| 135.51 g | of a 37.3% sodium acrylate solution in water (0.54 mol) |
| 28 g | of polyethylene glycol diacrylate of polyethylene glycol of molar mass 400 |
| 21.33 g | of a 15% aqueous solution of an addition product of 80 mol of ethylene oxide to 1 mol of a linear saturated C$_{16}$C$_{18}$ fatty alcohol |
| 65.70 g | of water |

To this solution were added with ice cooling 400.90 g (2.69 mol) of triethanolamine such that the internal temperature did not rise above 16° C. To the aqueous mixture was then added 1.0% by weight (4.8 g), based on monomers, of apple fiber (Bio-Apfelfaser AF 400, ex J. Rettenmaier & Söhne GmbH & Co, Germany). The solution obtained was transferred into a pressure vessel and saturated therein with carbon dioxide at 12 bar for 25 min. 26.67 g of a 3% aqueous solution of 2,2'-azobis(2-amidinopropane) dihydrochloride were added under pressure and homogeneously mixed in by raising the pressure. This was followed by passing carbon dioxide through the reaction mixture for a further 5 min. The saturated reaction mixture was expressed at 12 bar through a die 1 mm in diameter to form a free-flowing fine-cell foam.

The monomer foam obtained was applied to an A3-size glass plate having rims 3 mm high and was covered with a second glass plate. The foam sample was irradiated simultaneously from both sides with two UV/VIS radiators (UV 1000 from Höhnle) for 4 minutes.

The foam layer obtained was fully dried in a vacuum drying cabinet at 70° C. and subsequently adjusted to a moisture content of 5% by spraying with water.

| | |
|---|---|
| Solids content of reaction mixture: | 82.13% |
| Degree of neutralization: | 60 mol % |
| Monomer foam density: | 0.22 gcm$^{-3}$ |
| Polymer foam density: | 0.17 gcm$^{-3}$ |
| Foam structure: | homogeneous, fully open-cell, no skin |

Further properties of the open-cell foam are reported in Tables 4 and 5.

TABLE 4

| Example | Teabag test (FSC) [g/g] | CRC [g/g] | FSR [g/gsec] |
|---|---|---|---|
| Inventive 10 | 43.7 | 10.1 | 1.74 |
| Inventive 11 | 55.2 | 8.1 | 6.68 |

TABLE 5

| Example | Swollen foam thickness [mm] | CSA [mm$^2$] | Wet Failure Point [g] | WFV [g/mm$^2$] |
|---|---|---|---|---|
| Inventive 10 | 6.62 | 231.7 | 89.6 | 0.387 |
| Inventive 11 | 9.31 | 325.8 | 58.8 | 0.180 |

We claim:

1. A superabsorbent foam comprising from 0.1 to 5% by weight of a natural fiber selected from the group consisting of apple fiber, orange fiber, tomato fiber, wheat fiber, oat fiber, and mixtures thereof; said superabsorbent foam obtainable by foaming a polymerizable aqueous mixture comprising at least 50 mol% neutralized acid-functional monoethylenically unsaturated monomer or at least one basic polymer, a crosslinker, the natural fiber, and at least one surfactant, and subsequently polymerizing and/or crosslinking the foamed mixture.

2. The superabsorbent foam of claim 1 wherein the foam is surface postcrosslinked.

3. The superabsorbent foam of claim 1 wherein the polymerizable aqueous mixture comprises at least a 50% aqueous sodium or potassium hydroxide solution neutralized acrylic acid, a crosslinker containing at least two ethylenically unsaturated double bonds, a radical-forming initiator, the natural fiber, and at least one surfactant.

4. The superabsorbent foam of claim 1 wherein the polymerizable aqueous mixture comprises at least one basic polymer selected from the group consisting of polymers containing vinylamine units, polymers containing vinylguanidine units, polymers containing dialkylaminoalkyl(meth)acrylamide units, polyethyleneimines, ethyleneimine-grafted polyamidoamines, and polydiallyldimethylammonium chlorides.

5. An article comprising the superabsorbent foam of claim 1.

6. The article of claim 5 selected from the group consisting of a hygiene article to absorb body fluids, a dressing article to cover wounds, and a ventilation system filter.

7. A method of dewatering a liquid comprising contacting the liquid with a superabsorbent foam of claim 1.

8. The method of claim 7 wherein the liquid is a sludge or a water-containing oil or hydrocarbon.

9. A sealing or packaging material comprising a superabsorbent foam of claim 1.

10. A soil adjuvant comprising a superabsorbent foam of claim 1.

11. A method of thickening an aqueous liquid to facilitate disposal thereof, comprising admixing the aqueous liquid with a superabsorbent foam of claim 1 to thicken the aqueous liquid.

12. A superabsorbent foam comprising at least one natural fiber selected from the group consisting of apple fiber, orange fiber, tomato fiber, wheat fiber, oat fiber, and mixtures thereof;
    said superabsorbent foam obtainable by foaming a polymerizable aqueous mixture comprising at least a 50 mol% neutralized acid-functional monoethylenically unsaturated monomer or at least one basic polymer, a crosslinker, the natural fiber, and at least one surfactant, and subsequently polymerizing and/or crosslinking the foamed mixture,
    wherein the polymerizable aqueous mixture contains from 0.05 to 5% by weight of natural fiber, based on the monomer.

13. The superabsorbent foam of claim 12 further comprising from 1% to 60% water, by weight of the superabsorbent foam.

14. A process for producing a superabsorbent foam having improved wet strength, which comprises foaming a crosslinkable aqueous mixture comprising at least a 50 mol% neutralized acid-functional monoethylenically unsaturated monomer or at least one basic polymer, a crosslinker, a natural fiber selected from the group consisting of apple fiber, orange fiber, tomato fiber, wheat fiber, and mixtures thereof, and at least one surfactant, and subsequently polymerizing the monomer in the foamed mixture or crosslinking the basic polymer in the foamed mixture to form a hydrogel foam, wherein the aqueous mixture comprises from 0.1 to 5% by weight of the natural fiber.

15. The process of claim 14 wherein the foaming of the aqueous polymerizable mixture is effected by dissolving an inert gas in the mixture at from 2 to 400 bar and subsequently decompressing the mixture to atmospheric.

* * * * *